(12) United States Patent
Morries et al.

(10) Patent No.: US 10,905,897 B2
(45) Date of Patent: *Feb. 2, 2021

(54) SYNERGISTIC TREATMENT METHODOLOGIES USING LIGHT THERAPY

(71) Applicant: Neuro-Laser Foundation, Inc., Centennial, CO (US)

(72) Inventors: Larry Dwayne Morries, Lakewood, CO (US); Theodore Alan Henderson, Centennial, CO (US)

(*) Notice: Subject to any disclaimer, the term of this patent is extended or adjusted under 35 U.S.C. 154(b) by 249 days.

This patent is subject to a terminal disclaimer.

(21) Appl. No.: 15/960,281

(22) Filed: Apr. 23, 2018

(65) Prior Publication Data

US 2018/0236262 A1   Aug. 23, 2018

Related U.S. Application Data

(63) Continuation-in-part of application No. 15/299,448, filed on Oct. 20, 2016, now Pat. No. 9,950,189.

(51) Int. Cl.
*A61N 5/06* (2006.01)
*A61K 31/135* (2006.01)
*A61N 5/067* (2006.01)

(52) U.S. Cl.
CPC .......... *A61N 5/0618* (2013.01); *A61K 31/135* (2013.01); *A61N 5/0622* (2013.01); *A61N 2005/067* (2013.01); *A61N 2005/0659* (2013.01)

(58) Field of Classification Search
None
See application file for complete search history.

(56) References Cited

U.S. PATENT DOCUMENTS

| | | | | |
|---|---|---|---|---|
| 4,633,866 A * | 1/1987 | Peyman | ................... | A61F 9/008 606/3 |
| 4,671,254 A * | 6/1987 | Fair | ......................... | A61B 18/20 128/898 |
| 5,019,076 A * | 5/1991 | Yamanashi | ........... | A61B 18/082 606/45 |
| 5,580,555 A * | 12/1996 | Schwartz | ................. | A61P 27/16 424/85.1 |
| 9,238,150 B2 * | 1/2016 | Deisseroth | ......... | A61K 41/0057 |
| 9,259,432 B1 * | 2/2016 | Vig | ....................... | A61K 31/704 |
| 9,423,237 B2 * | 8/2016 | Milner | ............... | A61B 1/00096 |
| 10,420,918 B2 * | 9/2019 | Rodgers | .............. | A61M 27/002 |

(Continued)

OTHER PUBLICATIONS

Morries et al., Treatments for traumatic brain injury with emphasis on transcranial near-infrared laser phototherapy, Neuropsychiatric Disease and Treatment 2015:11 2159-2175 (Year: 2015).*

*Primary Examiner* — Carl H Layno
*Assistant Examiner* — Manolis Pahakis

(57) ABSTRACT

A treatment method for a variety of neurological conditions using a novel combination of near infrared (NIR) light therapy and the pharmacological agent ketamine. After administration of ketamine to a patient, NIR is aimed through the scalp at the brain, preferably targeted at the brain regions most affected. In addition, certain dietary supplements and an exercise program may be offered. Combined, these therapies have proved much more effective than the sum of their individual efficacies.

27 Claims, 2 Drawing Sheets

(56) References Cited

U.S. PATENT DOCUMENTS

| | | | | |
|---|---|---|---|---|
| 2004/0147501 A1* | 7/2004 | Dolmans | A61K 31/555 | 514/185 |
| 2004/0171601 A1* | 9/2004 | Fukumura | A61K 41/0076 | 514/185 |
| 2005/0159662 A1* | 7/2005 | Imanishi | A61B 3/1025 | 600/473 |
| 2009/0254154 A1* | 10/2009 | De Taboada | A61N 5/0613 | 607/88 |
| 2010/0204762 A1* | 8/2010 | De Taboada | A61N 5/0613 | 607/89 |
| 2011/0098781 A1* | 4/2011 | Mantle | A61H 1/008 | 607/46 |
| 2011/0144723 A1* | 6/2011 | Streeter | A61N 5/0618 | 607/88 |
| 2011/0152249 A1* | 6/2011 | Borsook | A61P 25/24 | 514/217 |
| 2011/0178441 A1* | 7/2011 | Tyler | A61N 5/0622 | 601/2 |
| 2011/0230701 A1* | 9/2011 | Simon | A61N 1/40 | 600/9 |
| 2012/0041305 A1* | 2/2012 | Grissom | A61B 90/39 | 600/431 |
| 2012/0053449 A1* | 3/2012 | Moses | A61N 2/006 | 600/411 |
| 2012/0083647 A1* | 4/2012 | Scheinin | A61N 2/006 | 600/13 |
| 2012/0148975 A1* | 6/2012 | Brawn | A61C 7/00 | 433/24 |
| 2012/0232536 A1* | 9/2012 | Liu | A61N 5/0613 | 606/9 |
| 2012/0289869 A1* | 11/2012 | Tyler | A61B 5/04008 | 601/2 |
| 2012/0296569 A1* | 11/2012 | Shahaf | A61B 5/4064 | 702/19 |
| 2013/0041309 A1* | 2/2013 | Siegel | A61B 18/203 | 604/20 |
| 2014/0121636 A1* | 5/2014 | Boyden | A61B 90/11 | 604/506 |
| 2014/0148636 A1* | 5/2014 | Best | A61P 27/16 | 600/9 |
| 2015/0094600 A1* | 4/2015 | Grutzendler | A61B 5/4064 | 600/476 |
| 2015/0174406 A1* | 6/2015 | Lamensdorf | A61N 1/36017 | 607/62 |
| 2016/0008628 A1* | 1/2016 | Morries | A61N 5/0622 | 607/89 |
| 2016/0183859 A1* | 6/2016 | Hartung | A61B 5/6821 | 600/321 |
| 2017/0100037 A1* | 4/2017 | Harmelin | G01N 21/6456 | |
| 2017/0143934 A1* | 5/2017 | Tsai | A61M 21/00 | |
| 2017/0191893 A1* | 7/2017 | Wang | B23K 26/361 | |
| 2017/0216595 A1* | 8/2017 | Geva | A61N 1/36139 | |

* cited by examiner

SYNERGISTIC TREATMENT METHODOLOGIES USING LIGHT THERAPY

This Application is a CIP of U.S. application Ser. No. 15/299,448, filed Oct. 20, 2016, now U.S. Pat. No. 9,950,189.

TECHNICAL FIELD

The present invention relates generally to deficiencies of neurotrophic factors in the tissues and related mitochondrial dysfunction; to disease states such as injury, disease, and dysfunction of the brain, spinal cord and/or nerves; neurodegeneration; neuro-muscular injuries and diseases; pain; and/or orthopedic and sports related injuries which are related to neurotrophic deficiencies and to mitochondrial dysfunction; and more particularly, to novel treatment methodologies using light therapy alone and/or in combination with specific pharmacological agents to stimulate neurotrophic factor production and mitochondrial repair which fundamentally underlie these injuries, diseases and/or dysfunctions. The present invention also relates to the localization of injury, disease, or dysfunction using the quantitative analysis of imaging or neurophysiological data; and using said localization to accurately target the application of light therapy to the correct area of damage and/or dysfunction. In certain embodiments, quantitative analysis of imaging or neurophysiological data would provide a method of measuring progression of therapeutic benefit of said therapeutic treatment in a manner heretofore not described.

BACKGROUND

The novel treatment methodologies of the present invention can be utilized to treat deficiencies of neurotrophic factors in the tissues and related mitochondrial dysfunction. A large number of health issues can result from deficiencies of neurotrophic factors in the tissues and/or subsequent mitochondrial dysfunction. These health issues can include, but not limited to: Traumatic Brain Injury (TBI); Idiopathic Parkinson's Disease (IPD); Alzheimer's Disease, Senility, and Dementia (ADSD); Post-Traumatic Stress Disorder (PTSD); Depression and Anxiety (DA); Multiple sclerosis (MS); and Spinal Cord Injuries (SCI), stroke (STR), neuropathy/polyneuropathy (PNL), pain, and/or radiculopathy/radiculitis (RDL). Mitochondrial dysfunction leads to a decrease in adenine triphosphate (ATP) production and loss of regulation of genetic, growth, and neuronal support functions. Infrared light has been shown to stimulate many of these essential mitochondrial functions. The current list of mitochondria dysfunction in health and disease is advancing. Disorders such as bipolar disease, dementia, AD, epilepsy, migraine headaches, strokes, neuropathic, IPD, cardiomyopathy, coronary artery disease, chronic fatigue syndrome, fibromyalgia, and diabetic neuropathy all have underlying pathophysiological mechanisms in common, resulting in mitochondrial dysfunction (Pieczenik, 2015). Fundamental to these disorders also are decreased or suppressed production of neurotrophic factors, including, but not limited to, nerve growth factor (NGF), brain-derived neurotrophic factor (BDNF), glial-derived neurotrophic factor (GDNF) and/or ciliary neurotrophic factor (CNTF), among others.

Furthermore, the correct identification of the brain-related disorder; or of the area of the brain involved by any given disorder; or the specific peripheral nerves affected by any given neuropathy/polyneuropathy, and/or radiculopathy/radiculitis, requires appropriate use of neuroimaging technology and/or peripheral nerve testing. Targeting of any non-systemic intervention including, but not limited to, the application of forms of electromagnetic radiation, require quantitative analysis of said neuroimaging and/or peripheral nerve testing. Targeting treatments to specific areas of the brain or body which are injured or disordered, using these modalities, is fundamental to this claim.

A number of clinically important and demographically prevalent disorders have proven to be products of neurotrophin deficiency and related mitochondrial dysfunction.

Traumatic Brain Injury

The Centers for Disease Control and Prevention estimated that 1.5 million Americans sustained TBI annually in 2000. As of 2006, the estimates had risen to 1.7 million brain injuries annually. Undoubtedly, these point prevalence proportions will increase as military personnel return home and the problem of repeated mild TBI (mTBI) becomes more recognized in sports. Current estimates of the prevalence of TBI among Veterans range from 9.6% to 20%, with an estimated total of more than 300,000 cases of TBI among military personnel since 2000. The current estimates of the combined number of sports-related concussions and brain injuries in the United States are 1.6-3.8 million annually.

TBI results in a wide spectrum of neurological, psychiatric, cognitive, and emotional consequences. In part, the variation is related to the severity of the injury (mild, moderate, severe TBI), which are stratified based on Glascow Coma score, periods of unconsciousness, and degrees of amnesia. Furthermore, the diversity of sequalae can be related to the areas of the brain that are injured, the severity of the injury (highly variable within the classification of "mild" and "moderate"), and the evolution of the injury over time due to neuro-inflammatory processes.

TBI disrupts membrane function and gives rise to early ionic and neurotransmitter perturbations (Veech R L, The mitochondrial permeability transition pore provides a key to the diagnosis and treatment of traumatic brain injury. *IUBMB Life.* 2012; 64(2):203-7, 2012; incorporated in its entirety by reference herein). Together with a substantial release of the excitatory neurotransmitter glutamate, these perturbations initiate a cascade of events that extensively disrupts normal cellular function, alters glucose metabolism, suppresses neurotrophin expression, induces free radical production, and impairs mitochondrial function (Veech R L, et al., 2012; Barkhoudarian G, et al., The molecular pathophysiology of concussive brain injury. *Clin Sports Med.;* 30(1):33-48; 2011; Prins M, et al., The pathophysiology of traumatic brain injury at a glance. *Dis Model Mech.* 2013; 6(6):1307-15; 2013; Cheng G, et al., Mitochondria in traumatic brain injury and mitochondrial-targeted multipotential therapeutic strategies. *Br J Pharmacol.* 2012; 167(4):699-719; 2012; each incorporated in its entirety by reference herein). Calcium ($Ca^{2+}$) begins to accumulate within neurons and significantly impairs function. Increased intracellular $Ca^{2+}$ activates mitochondrial uptake, leading to $Ca^{2+}$ overload in mitochondria (Veech et al., 2012), oxidative stress, and impaired mitochondrial function or mitochondrial death (Prins M, et al., 2013; Cheng G, et al., 2012; Xiong Y, et al., Mitochondrial dysfunction and calcium perturbation induced by traumatic brain injury. *J Neurotrauma.* 14(1):23-34; 1997; each incorporated herein in its entirety by reference). Accumulations of $Ca^{2+}$ can directly destroy portions of the diverse mitochondrial population (Lifshitz J, et al., Structural and functional damage sustained by mitochondria after traumatic brain injury in the rat:

evidence for differentially sensitive populations in the cortex and hippocampus. *J Cereb Blood Flow Metab.* 23(2):219-31; 2003; incorporated in its entirety by reference herein) and induce persistent damage in surviving mitochondria (Lifshitz J, et al., Mitochondrial damage and dysfunction in traumatic brain injury. *Mitochondrion;* 4(5-6):705-13; 2004; incorporated in its entirety by reference herein). In addition, increased free radical production, disruption of nitric oxide pathways, and deficiencies in glucose compound the situation.

In contrast to acute TBI, neurophysiological dysfunction in chronic TBI is less well understood. It is clear, that mechanisms activated in acute TBI, such as neuronal injury and apoptosis, would have persistent consequences. Studies have shown that diffuse and Wallerian white matter degeneration occurs following TBI. In many ways, stroke and TBI share these long-term mechanisms (Leker R R, Shohami E. Cerebral ischemia and trauma-different etiologies yet similar mechanisms: neuroprotective opportunities. *Brain Res Brain Res Rev.* 2002; 39(1):55-73, 2002; incorporated in its entirety by reference herein). Suppression of or impaired production of neurotrophins following injury underlies and/or exacerbates the sequalae of acute injury. Neurotrophin deficiency may lead to loss or dysfunction of mitochondria, neuronal cell death, synaptic degeneration, loss of dendrites or dendritic dearborization, and loss of neuronal circuits. Long-term disruption of mitochondrial membranes by lipid peroxidation, disrupted $Ca^{2+}$ regulation, loss of subpopulations of mitochondria, and reduced energy production can continue long past the acute phase of TBI (Naviaux R K. Metabolic features of the cell danger response. *Mitochondrion.* 2014; 16:7-17, 2014; incorporated in its entirety by reference herein). In humans, impaired mitochondrial function may persist for months to years based on observations of decreased glucose metabolism in patients using FDG PET (Lin A P, et al., Metabolic imaging of mild traumatic brain injury. *Brain Imaging Behav.* 2012; 6(2):208-23, 2012; incorporated in its entirety by reference herein). Decreased cerebral blood flow to the injured area also persists for many years based on perfusion single photon emission computed tomography (SPECT) scans (Raji C A, et al. Clinical utility of SPECT neuroimaging in the diagnosis and treatment of traumatic brain injury: a systematic review. *PLoS One.* 2014; 9(3):e91088, 2014; incorporated in its entirety herein by reference). Injured and disrupted axons, as well as altered proteolytic pathways in injured neurons and/or altered nitric oxide pathways, can lead to the accumulation of amyloid precursor proteins and tau proteins. Accumulations of these abnormal proteins can set in motion a sequence of pathophysiological processes leading to Alzheimer's disease, chronic traumatic encephalopathy, and Parkinson's disease. Blast injury may be particularly harmful, resulting in persistent axonal abnormalities of varicosities and accumulated abnormal proteins. Recent evidence has shown a strong correlation between persistent areas of disrupted white matter, shown by diffusion tensor imaging, and areas of decreased cerebral blood flow which were present at the time of injury. Fundamental to these prolonged consequences of TBI are decreased or suppressed production of neurotrophic factors, including, but not limited to, BDNF. Fundamental to these prolonged consequences of TBI are decreased or suppressed function of mitochondria.

Patients with TBI can experience: headaches, visual disturbances, dizziness, cognitive impairment, loss of executive skills, memory impairment, fatigue, impulsivity, impaired judgment, emotional outbursts, anxiety, and depression. The situation can be further clouded by secondary and/or comorbid post-traumatic stress disorder (PTSD), depression, and anxiety, which can have symptoms that overlap with those described above and appear to be increasingly likely with repetitive concussive or subconcussive brain injury.

Idiopathic Parkinson's Disease

Idiopathic Parkinson's disease (IPD) is a progressive neurological disorder characterized by selective degeneration of dopaminergic neurons in the substantia nigra. Manifestations of clinical symptoms often do not occur until at least 60% of substantia nigra neurons are lost and/or dopaminergic integrity is reduced significantly. While IPD may be the most prevalent form of parkinsonism, it shares, in part, symptoms with progressive supranuclear palsy (PSP), multiple system atrophy (MSA), vascular parkinsonism, and dementia with Lewy bodies. Symptoms of tremor, bradykinesia, postural instability, rigidity, and autonomic dysfunction can overlap, to a greater or lesser degree, in each of these disorders. Specific clinical symptoms, such as cerebellar signs in MSA, gaze palsy in progressive supranuclear palsy, or overt dementia and visual hallucinations in dementia with Lewy bodies, may only manifest at a later stage of the disease. Given the multifarious presentation of IPD, the discrimination of these diseases early in the course of illness can be challenging. Yet, the correct diagnosis is critical, as each disease process has a different pathology, different progression, and different response to medication. Neuroimaging has a critical role in the differential diagnoses of these disorders (Henderson, 2013).

Mitochondrial damage is the central event that triggers apoptosis in neurons. The role of mitochondrial dysfunction in PD was directly demonstrated by the discovery of the MPTP-induced acute Parkinsonism in young subjects. Similarly, other PD causing toxins such as rotenone also cause neurodegeneration via selective inhibition of mitochondrial function. This has led to the generation of animal models which have been used to study mitochondrial dysfunction and other effect of environmental toxins (Mythri R B, et al., Mitochondrial complex I inhibition in Parkinson's disease: how can curcumin protect mitochondria? Antioxid Redox Signal. 9(3):399-408, 2007; incorporated in its entirety by reference herein).

Deficiencies of BDNF have been strongly implicated in the pathogenesis and progression of IPD (Hyman C, et al., BDNF is a neurotrophic factor for dopaminergic neurons of the substantia nigra. Nature. 21; 350(6315):230-2, 1991; Levivier M, et al., Intrastriatal implantation of fibroblasts genetically engineered to produce brain-derived neurotrophic factor prevents degeneration of dopaminergic neurons in a rat model of Parkinson's disease. J Neurosci. 15(12):7810-20, 1995; Johnson M E, et al., Investigation of tyrosine hydroxylase and BDNF in a low-dose rotenone model of Parkinson's disease. J Chem Neuroanat. 70:33-41, 2015; Bathina S, Das U N. Brain-derived neurotrophic factor and its clinical implications. Arch Med Sci. 11(6): 1164-78, 2015; each incorporated in its entirety by reference herein). BDNF is a critical neurotrophic factor for dopaminergic neurons and has been shown to rescue dopaminergic neurons in animal models of IPD. Augmentation of BDNF can lead to functional recovery in animal models of IPD. A direct correlation between serum BDNF levels and degree of functional and/or cognitive impairment has been shown in humans (Bialecka M, et al., BDNF G196A (Val66Met) polymorphism associated with cognitive impairment in Parkinson's disease. Neurosci Lett. 561:86-90, 2014; incorporated in its entirety by reference herein). Attempts to increase BDNF through exercise have yielded slight, but measurable increases, and have been associated with clinical improvement (Marusiak J, et al., Interval training-induced alleviation of rigidity and hypertonia in patients with Parkinson's disease is accompanied by increased basal serum brain-derived neurotrophic factor. J Rehabil Med. 47(4): 372-5, 2015; Angelucci F, et al., The effects of motor rehabilitation training on clinical symptoms and serum BDNF levels in Parkinson's disease subjects. Can J Physiol Pharmacol. 10:1-7, 2016; each incorporated in its entirety by reference herein).

Alzheimer's Disease, Senility, and Dementia

Between 1997 and 2025, the number of individuals worldwide over 65 years of age will increase from 381 million to 823 million. Age-related conditions can be expected to increase in frequency as the population ages. In particular, the dementias, such as Alzheimer's disease (AD), frontotemporal dementia (FTD), dementia with Lewy bodies (DLB), vascular dementia (VaD), and other stroke-related disorders, will increase in frequency, and those afflicted will place increasing demands on medical systems and on families. The frequency of dementias doubles with every 5 years of age over 60. Without effective treatment, the number of persons with dementing illnesses will quadruple in the next 50 years. Worldwide, an estimated 81 million people will have some form of dementia. The number of people with AD in the United States alone, currently approximately 5 million, is expected to exceed 13 million by 2050. In addition, 19% of those over the age of 65 years develop mild cognitive impairment (MCI) which also is referred to as senility or early dementia. It is a potential precursor to a dementia. It is estimated that approximately 156 million persons worldwide will be affected by MCI. Neuroimaging, particularly SPECT neuroimaging with quantitative analysis, has a critical role in the early diagnoses of these disorders with an accuracy in the high 80% range (Henderson, 2013).

Furthermore, new medications in development—some of which will target amyloid accumulations, such as gamma and b secretase inhibitors/modulators, as well as alpha secretase activators and tau kinase inhibitors—are relatively unlikely to clear a large burden of amyloid such as is found in late disease and even less likely to reverse the pathology when secondary events (such as inflammation) have occurred. Indeed, in August 2010, Eli Lilly halted clinical trials of a gamma secretase inhibitor due to lack of effect on cognitive function. While this pharmaceutical was apparently effective in reducing amyloid deposits in the form of plaques, subjects showed marked worsening of cognitive function. Currently, there are no effective treatments for Alzheimer's disease or the other dementias. Only mitigative and palliative care can be offered.

Recent studies of postmortem brains from AD patients and transgenic AD mice suggest that oxidative damage, induced by amyloid beta, is associated with mitochondria dysfunction early in AD progression. Amyloid beta and amyloid precursor protein are known to localize to mitochondrial membranes, blocking the transport of nuclear-encoded mitochondrial proteins to mitochondria, interacting with mitochondrial proteins, disrupting the electron transport chain, increasing reactive oxygen species production, causing mitochondrial damage and, ultimately, preventing neurons from functioning normally. Mitochondria are the major source of energy for the brain. The accumulation of mitochondrial DNA (mtDNA) changes may increase reactice oxygen species (ROS) production and reduce mitochondrial ATP in an age-dependent manner (Reddy P H. Mitochondrial dysfunction in aging and Alzheimer's disease: strategies to protect neurons. Antioxid Redox Signal. 9(10): 1647-58, 2007; incorporated in its entirety by reference herein).

Evidence has shown a direct relationship between low levels of brain-derived neurotrophic factor (BDNF) and high cellular amyloid burden in Alzheimer's disease models. Patients with lower BDNF levels also show worse verbal processing skills. Mitochondrial dysfunction is seen to be the fundamental link between neurotrophin levels and cellular toxicity, neuronal death, and circuitry failure which are the neurological underpinnings of Alzheimer's disease. Higher brain BDNF expression has been associated with slower cognitive decline and may also reduce the deleterious effects of AD pathology on cognitive decline (Buchman A S, et al., Higher brain BDNF gene expression is associated with slower cognitive decline in older adults. Neurology. 86(8): 735-41, 2016; incorporated in its entirety by reference herein).

We and others have explored the neuroprotective and regenerative properties of NIR light (Johnstone and colleagues, Turning on lights to stop neurodegeneration: The potential of near infrared light therapy in Alzheimer's and Parkinson's disease. Frontiers in Neurosci. 9:500, 2016; incorporated in its entirety by reference herein). Early evidence shows the NILT can prevent neuronal death and atrophy in models of Alzheimer's disease.

Post-Traumatic Stress Disorder

Post-traumatic stress disorder (PTSD) is a mental health condition which is triggered by either experiencing or witnessing a terrifying event. Recent evidence has shown that certain genes increase the vulnerability to PTSD. Symptoms may include nightmares, intrusive thoughts about the traumatic event, severe anxiety, and episodes of reliving the traumatic event (flashbacks). Symptoms may start within three months of an event, but also may not appear until years after the event. In addition to symptoms may include efforts to avoid people, places and things that are reminders of the event, irritability, emotional numbness, loss in interest and pleasure in usual activities, social withdrawal, mood change, memory problems, relationship problems, guilt and shame.

Recent studies of combat Veterans have revealed persistent mitochondrial dysfunction. Mitochondrial DNA copy number (mtDNAcn) in blood cells is an emerging systemic index of mitochondrial biogenesis and function. In a study of combat veterans with and without PTSD, mtDNAcn was significantly lower in subjects with PTSD. This study provides the first evidence of mtDNAcn in combat PTSD. Altered mtDNAcn in PTSD may reflect impaired energy metabolism, which represent a novel aspect of its pathophysiology (Bersani F S, et al., Mitochondrial DNA copy number is reduced in male combat veterans with PTSD. Prog Neuropsychopharmacol Biol Psychiatry. 64:10-7, 2016; incorporated in its entirety by reference herein).

Multiple studies have found BDNF serum levels to be decreased in those suffering from PTSD (Dell'Osso L, et al., Brain-derived neurotrophic factor plasma levels in patients suffering from post-traumatic stress disorder. Prog Neuropsychopharmacol Biol Psychiatry. 33(5):899-902, 2009; Kaplan G B, et al., Brain-derived neurotrophic factor in traumatic brain injury, post-traumatic stress disorder, and their comorbid conditions: role in pathogenesis and treatment. Behav Pharmacol. 21(5-6):427-37, 2010; each incorporated in its entirety by reference herein). BDNF-mediated mechanisms are asserted to be critical to the neurobiological processes underlying the symptoms of PTSD (Mahan A L, Ressler K J. Fear conditioning, synaptic plasticity and the amygdala: implications for posttraumatic stress disorder. Trends Neurosci. 35(1):24-35, 2012; incorporated in its entirety by reference herein).

Depression

Depression is a profound problem in American and worldwide. Depression is more than "having a bad day" or "feeling blue". It is a long-lasting experience of low mood, loss of enjoyment in life, loss of interest, low energy, changes in sleep and/or appetite, and a decrease in one's ability to think clearly (cognition). Many people with depression experience extreme distress and anguish. Some feel suicidal and may act on those impulses. Depression is found in every country of the world and in every socioeconomic class. The rate of depression worldwide and in America is about 5-7%.

Depression is associated with a loss of neurons, reduced synapse numbers, and dearborization of dendrites in the hippocampus and frontal cortices (Cook S C, Wellman C L Chronic stress alters dendritic morphology in rat medial prefrontal cortex. J Neurobiol 60(2):236-48, 2004; Morais M, et al., The effects of chronic stress on hippocampal adult neurogenesis and dendritic plasticity are reversed by selective MAO-A inhibition. J Psychopharmacol 28(12):1178-83, 2014; Duman R S, Pathophysiology of depression and innovative treatments: remodeling glutamatergic synaptic connections. Dialogues Clin Neurosci 16(1):11-27, 2014; each incorporated in its entirety by reference herein). In essence, depression is a model of reversible neurodegeneration. Key neurotrophic factors are decreased in depression, such as, but not limited to, brain-derived neurotrophic factor (BDNF). Currently available monoaminergic antidepressants can potentially upregulate BDNF (Engel D, et al., Chronic administration of duloxetine and mirtazapine downregulates proapoptotic proteins and upregulates neurotrophin gene expression in the hippocampus and cerebral cortex of mice. J Psychiatr Res 47(6):802-8, 2013; incorporated in its entirety by reference herein), which increases neural progenitor cells in the hippocampus of rodent models (Duman 2014) and human. Methods of preventing neurogenesis, such as focal irradiation or focal knockdown of the BDNF expression can prevent the behavioral response to monoaminergic antidepressants. Similarly, deficiencies in neurotrophic factors can lead to denudation of dendritic arbors in animal models of stress (Cook and Wellman, 2004) and dendritic spine density markedly decreases (Duman and Duman, Spine synapse remodeling in the pathophysiology and treatment of depression. *Neurosci Lett* 601:20-9, 2015; incorporated in its entirety by reference herein). Evidence supports the effect of these antidepressants is to weakly increase neurotrophic factors and improve mitochondrial function. These changes are manifested grossly since the size of the hippocampus is reduced in patients with depression based on MRI. Hippocampal volume briefly enlarges following ECT treatment for depression (Nordanskog P, Larsson M R, Larsson E M, Johanson A (2014) Hippocampal volume in relation to clinical and cognitive outcome after electroconvulsive therapy in depression. Acta Psychiatr Scand 129(4):303-11, 2014; incorporated in its entirety by reference herein). Monoaminergic antidepressants do not induce hippocampal enlargement (Godlewska et al., Short-term escitalopram treatment and hippocampal volume. Psychopharmacology (Berl) 231(23):4579-81, 2014; incorporated in its entirety by reference herein). The role of mitochondrial dysfunction in depression was recently reviewed (Kambe Y, Miyata A. Potential involvement of the mitochondrial unfolded protein response in depressive-like symptoms in mice. Neurosci Lett. 19; 588:166-71, 2015; incorporated in its entirety by reference herein).

Anxiety

Anxiety is an exaggeration of the normal mental and physical sensations of fear. Anxiety can manifest as fears, nervousness, restlessness, worries, uncertainty, irritability, and trouble concentrating. In children, anxiety can be confused with ADHD, because of restlessness and trouble focusing. Anxiety also can produce physical symptoms, such as trembling, upset stomach, nausea, diarrhea, headache, chest pain, trouble breathing, irregular heartbeats, muscle tension, and sleep disturbance. These physical symptoms are particularly likely during severe anxiety or panic attacks. Actually, anxiety is a general term for several disorders that produce fear, apprehension, or worry. This includes Social Anxiety Disorder, Panic Disorder, Obsessive Compulsive Disorder, Separation Anxiety Disorder, Post-Traumatic Stress Disorder, and Generalized Anxiety Disorder. Approximately 27% of Americans suffer from one form of anxiety or another.

Research has shown that abnormal levels of certain neurotrophic factors are markedly decreased in people with anxiety disorders and in animal models of anxiety. Decreased levels of BDNF are associated with exaggerated fear responses (Yee B K, et al., Levels of neurotrophic factors in the hippocampus and amygdala correlate with anxiety- and fear-related behaviour in C57BL6 mice. J Neural Transm (Vienna). 114(4):431-44, 2007; Martinowich K, et al., New insights into BDNF function in depression and anxiety. Nat Neurosci. 10(9):1089-93, 2007; each incorporated in its entirety by reference herein), more severe PTSD symptoms, and greater accumulated neurological damage from stress. Similarly, decreased corticotrophin releasing factor (CRF) is associated with increased anxiety (Hauger R L, et al. Role of CRF receptor signaling in stress vulnerability, anxiety, and depression. Ann NY Acad Sci. 1179: 120-43, 2009; incorporated in its entirety by reference herein) Enhancement of neurotrophic factor levels can reduce or prevent anxiety in animal models (Govindarajan A, et al., Transgenic brain-derived neurotrophic factor expression causes both anxiogenic and antidepressant effects. Proc Natl Acad Sci USA. 103(35):13208-13, 2006; incorporated in its entirety by reference herein) Enhanced neurotrophic activity has a direct influence on mitochondrial health and activity. Treatments for anxiety disorders include medications, a variety of therapy techniques, physical exercise, and even certain supplements. Some medications for anxiety, such as the benzodiazepines, are addictive and interfere with learning and memory function. Other medications which are often prescribed for anxiety, the SSRI's, can actually worsen anxiety in some patients. No single medication seems to be effective for all patients with anxiety disorders. Many patients with anxiety find only partial relief with currently available medications. Recent clinical work with ketamine, which powerfully upregulates BNDF and other neurotrophins, has shown benefit in anxiety (Ballard E D, et al., Improvement in suicidal ideation after ketamine infusion: relationship to reductions in depression and anxiety. J Psychiatr Res. 58:161-6, 2014; incorporated in its entirety by reference herein) and PTSD (Feder A, et al., Efficacy of intravenous ketamine for treatment of chronic posttraumatic stress disorder: a randomized clinical trial. JAMA Psychiatry. 71(6):681-8, 2014; incorporated in its entirety by reference herein). Alone or in combination with NILT, ketamine could be utilized as an innovative and effective anxiety treatment.

Multiple Sclerosis

Multiple sclerosis (MS) is a neurological disease in which elements of the immune system attacks the protective sheath (myelin) that covers axons in the spinal cord and brain. Ultimately, the nerves themselves may degenerate and die. Signs and symptoms vary widely, depending on where in the central nervous system the damage occurs, the amount of damage, and which nerves are affected. Symptoms can include impaired motor function, alertness, cognitive function, or emotional control. There currently is no cure for multiple sclerosis. However, current treatments can help quicken recovery from attacks, modify the course of the disease, and mitigate or palliate symptoms.

Degeneration of chronically demyelinated axons is a major cause of irreversible neurological disability in MS patients. We propose a hypothesis that mitochondria play a key role in this chronic axonal loss. Following demyelination there is redistribution of sodium channels along the axon and mitochondria are recruited to the demyelinated regions to meet the increased energy requirements necessary to maintain conduction. The mitochondria present within the chronically demyelinated axons will be functioning at full capacity. The axon may well be able to function for many years due to the adaptive mechanisms but eventually, despite antioxidant defenses, free radical damage will accumulate and mitochondrial function will become compromised. ATP concentration with the axon will decrease and the effect on axonal function will be profound. The actual cause of cell death could be due to a number of mechanisms related to mitochondrial dysfunction, including, but not limited to, failure of ionic homeostasis, calcium influx, mitochondrial mediated cell death or impaired axonal transport. It is likely mitochondrial dysfunction is central to this process. BDNF has a critical role in the pathogenesis, progression, and treatment of MS (Sarchielli P, et al., Brain-derived neurotrophic factor in patients with multiple sclerosis. J Neuroimmunol. 132(1-2):180-8, 2002; Ziemssen T, et al., Glatiramer acetate-specific T-helper 1- and 2-type cell lines produce BDNF: implications for multiple sclerosis therapy. Brain-derived neurotrophic factor. Brain. 125 (Pt 11):2381-91, 2002; Caggiula M, et al., Neurotrophic factors in relapsing remitting and secondary progressive multiple sclerosis patients during interferon beta therapy. Clin Immunol. 118 (1):77-82, 2006; each incorporated in its entirety by reference herein). Standard treatments for MS include interferon beta, which powerfully upregulates BDNF and modulates interleukin-10 (Hamamcioglu K, Reder A T. Interferon-beta regulates cytokines and BDNF: greater effect in relapsing than in progressive multiple sclerosis. Mult Scler. 13(4): 459-70, 2007; incorporated in its entirety by reference herein). Efforts to upregulate BDNF are considered highly promising treatments for MS (Khorshid Ahmad T, et al., Transcriptional Regulation of Brain-Derived Neurotrophic Factor (BDNF) by Methyl CpG Binding Protein 2 (MeCP2): a Novel Mechanism for Re-Myelination and/or Myelin Repair Involved in the Treatment of Multiple Sclerosis (MS). Mol Neurobiol. 53(2):1092-107, 2016; incorporated in its entirety by reference herein). Nerve growth factor, another neurotrophin, also has been strongly implicated in the pathogenesis and treatment of MS (Acosta C M, et al., Exploring the role of nerve growth factor in multiple sclerosis: implications in myelin repair. CNS Neurol Disord Drug Targets. 12(8):1242-56, 2013; incorporated in its entirety by reference herein).

Spinal Cord Injury

A spinal cord injury signifies damage to any part of the spinal cord or nerves emerging from the spinal canal. This injury is largely irreversible with currently available treatments. The injury often causes permanent changes in movement, strength, sensation and other body functions. Injury to the spinal cord can be complete—involving all feeling and motor control below the level of the injury—or partial— leaving some sensation or motor control below the lesion. Depending on the level of the injury, spinal cord injuries may result in one or more signs and symptoms, such as loss of movement, loss of sensation, including the ability to feel heat, cold and touch, loss of bowel or bladder control, exaggerated reflexes, pain or an intense stinging sensations, and/or difficulty breathing, coughing or clearing secretions from the lungs.

Changes in mitochondrial morphology and function play an important role in secondary damage after acute spinal cord injury. At 2-24 hours after injury, malondialdehyde, cytochrome c levels and caspase-3 expression are increased, but glutathione content, adenosine triphosphate content, Na+-K+-ATPase activity and mitochondrial membrane potential are gradually reduced. Mitochondrial morphology is altered during the acute stage of spinal cord injury. Mitochondrial membrane potential and permeability are reduced in the acute state of injury. In summary, mitochondrial apoptosis is activated at time of spinal cord injury (Zhi-qiang Jia, et al., Time representation of mitochondrial morphology and function after acute spinal cord injury. Neur Regen Res. 11(1):24, 2016; incorporated in its entirety by reference herein).

The pathophysiological changes caused by secondary injury with regards to subcellular organelles, the time-related changes in mitochondrial morphology and function after acute SCI, and the secondary molecular events set in motion by mitochondrial dysfunction lay the foundation for a theoretical basis for mitochondria-targeted therapy for SCI, and provided a new target for the prevention and treatment of SCI.

Mild-to-Moderate Stroke (STR)

Stroke is the result of blockage or ischemia of the blood vessels to the brain. Stroke can vary from minor with only transient clinical impact to fatally severe. Mild-to-moderate stroke usually results in loss of some motor, sensory, and/or executive function accompanied by neurodegenerative changes. Currently, the treatment of stroke is limited to the acute setting within hours of the event or to physical rehabilitation. Treatments which improve brain function after stroke are sorely needed. Much of the mechanisms involved in the pathology of TBI apply to the pathology of stroke. The initial insult consists of an interruption of arterial bloodflow to a given portion of brain. This can result from occlusion of the artery (ischemic stroke) or due to bleeding from the blood vessel which compromises the artery's ability to deliver blood to the appropriate target portions of the brain (hemorrhagic stroke). Stroke disrupts membrane function and gives rise to early ionic and neurotransmitter perturbations (Veech R L, 2012). Together with a substantial release of the excitatory neurotransmitter glutamate, these perturbations initiate a cascade of events that extensively disrupts normal cellular function, alters glucose metabolism, suppresses neurotrophin expression, induces free radical production, and impairs mitochondrial function Veech R L, et al., 2012; Prins et al., 2013). An early event is increased release of potassium which is proportional to the severity of the injury (Prins et al., 2013). This has a robust inhibitory effect on neuronal activity. Calcium ($Ca^{2+}$) begins to accumulate within neurons and significantly impairs function. Increased intracellular $Ca^{2+}$ activates mitochondrial uptake, leading to $Ca^{2+}$ overload in mitochondria (Veech et al., 2012), oxidative stress, and impaired mitochondrial function or mitochondrial death (Prins M, et al., 2013; Xiong Y, et al., 1997). Accumulations of $Ca^{2+}$ can directly destroy portions of the diverse mitochondrial population (Lifshitz J, et al., 2003) and induce persistent damage in surviving mitochondria (Lifshitz J, et al., 2004). Glucose is the primary energy source for neurons, but can only be delivered by arterial blood flow. Following a stroke, the primary area which loses blood flow is deprived of oxygen and glucose. The area surrounding the primary area, referred to as the penumbra, experiences a severe deficit of oxygen and of glucose. This can be seen as a prolonged depression of both cerebral perfusion and cerebral glucose metabolism. Moreover, glucose appears to be shunted from mitochondrial pathways to the pentose phosphate pathway. Overall these changes create an energy crisis inside the affected neurons.

Additionally, this energy crisis promotes increased concentrations of free radicals, due to increased pentose phosphate metabolism, reduced mitochondrial function, and impaired free radical scavenger mechanisms. The consequences of increased free radicals can be far-reaching including propagation of additional free radicals, breakdown of lipids within membranes, edema, inflammation, and DNA damage. In many ways, stroke and TBI share these long-term mechanisms. As taught above, suppression of or impaired production of neurotrophins following stroke underlies and/or exacerbates the sequalae of acute stroke. Neurotrophin deficiency may lead to loss or dysfunction of mitochondria, neuronal cell death, synaptic degeneration, loss of dendrites or dendritic dearborization, and loss of neuronal circuits. Long-term disruption of mitochondrial membranes by lipid peroxidation, disrupted $Ca^{2+}$ regulation, loss of subpopulations of mitochondria, and reduced energy production can continue long past the acute phase of stroke. In humans, impaired mitochondrial function may persist for months to years based on observations of decreased glucose metabolism in patients using FDG PET. Decreased cerebral blood flow to the injured area also persists for many years based on perfusion SPECT scans (Ueda T, Yuh W T. Single-photon emission CT imaging in acute stroke. Neuroimaging Clin N Am. 15(3):543-51, 2005; Oku N, et al., Nuclear neuroimaging in acute and subacute ischemic stroke. Ann Nucl Med. 24(9):629-38, 2010; each incorporated in its entirety by reference herein). Fundamental to these prolonged consequences of stroke are decreased or suppressed production of neurotrophic factors, including, but not limited to, BDNF. Fundamental to these prolonged consequences of stroke are decreased or suppressed function of mitochondria.

Neuropathy/Polyneuropathy (PNL)

Neuropathy is a dysfunction of nerve transmission/nerve conduction in the peripheral nerves (usually the lower extremities). The most common cause is diabetes, but there are other etiological factors, such as carpal tunnel compression, spinal disc herniation, etc. Neuropathy can involve one or multiple nerves (polyneuropathy). It is generally mild-to-moderately disabling and/or can contribute to Restless Leg Syndrome. Currently, the treatment for neuropathy is prevention and then the pharmaceuticals, gabapentin or pregabalin, to treat the uncomfortable symptoms of numbness, tingling and pain. Note: these pharmaceuticals do nothing to restore the function of the nerve. We have shown that infrared light improves nerve conduction (i.e., improve function of the nerve) and reduces symptoms.

Diabetic PNL, is associated with the activation of apoptosis and mitochondrial dysfunction. Intact and acutely dissociated neurons from diabetic rats demonstrated decreased Bcl-2 levels and translocation of cytochrome C from the mitochondria to the cytoplasm. Apoptosis associated with mitochondrial dysfunction may contribute to the pathogenesis of diabetic sensory neuropathy (Srinivasan S, et al., Diabetic peripheral neuropathy: evidence for apoptosis and associated mitochondrial dysfunction. Diabetes. 2000 November; 49(11):1932-8, 2000; incorporated in its entirety by reference herein).

Over forty years of research has documented the role of neurotrophin deficiency in peripheral neuropathies (Apfel S C, et al., Nerve growth factor prevents toxic neuropathy in mice. Ann Neurol. 29(1):87-90, 1991; Wuarin L, et al., Early reduction in insulin-like growth factor gene expression in diabetic nerve. Exp Neurol. 130(1):106-14, 1994; Brewster W J, et al., Diabetic neuropathy, nerve growth factor and other neurotrophic factors. Trends Neurosci. 17(8):321-5, 1994; Verge V M, et al., Mechanisms of disease: role of neurotrophins in diabetes and diabetic neuropathy. Handb Clin Neurol. 126:443-60, 2014; each incorporated in its entirety herein by reference), in particular diabetic neuropathy (Hellweg R, Halting H D. Endogenous levels of nerve growth factor (NGF) are altered in experimental diabetes mellitus: a possible role for NGF in the pathogenesis of diabetic neuropathy. J Neurosci Res. 26(2):258-67, 1990; Schmidt R E. The role of nerve growth factor in the pathogenesis and therapy of diabetic neuropathy. Diabet Med. 10 Suppl 2:10S-13S, 1993; Dey I, et al., Diabetic Schwann cells suffer from nerve growth factor and neurotrophin-3 underproduction and poor associability with axons. Glia. 61(12):1990-9; 2013; each incorporated in its entirety by reference herein), but also many other forms of neuropathy (Sahenk Z, et al., AAV1.NT-3 gene therapy for charcot-marie-tooth neuropathy. Mol Ther. 22(3):511-21, 2014; Lasko L, et al., Multimodal assessment of nervous and immune system responses following sciatic nerve injury. Pain. 154(12):2782-93, 2013; Chowdhury S R, et al., Ciliary neurotrophic factor reverses aberrant mitochondrial bioenergetics through the JAK/STAT pathway in cultured sensory neurons derived from streptozotocin-induced diabetic rodents. Cell Mol Neurobiol. 34(5):643-9, 2014; each incorporated in its entirety by reference herein).

Radiculopathy/Radiculitis (RDL)

Radiculopathy is irritation to spinal cord nerve roots usually caused by some sort of direct traumatic event. Radiculitis results from irritation to the sensory nerve root resulting in pain. These can occur with almost any traumatic event, intervertebral disc disease, spinal compression, spinal stenosis, and other degenerative processes. Currently, treatment is limited to surgical intervention, spinal manipulation, pain medications, injections of steroids or opiates, physical therapy, and traction. None of these treatments, in and of themselves, restore nerve function, although surgical intervention can relieve pressure on the nerve; however, surgery has a recurrence rate of up to 50% over 5 years. The pathophysiology of intervertebral disc disease includes activation of mitochondrial-bound apoptosis regulating proteins (Chen J W, et al., The responses of autophagy and apoptosis to oxidative stress in nucleus pulposus cells: implications for disc degeneration. Cell Physiol Biochem. 34(4):1175-89, 2014; Gruber H E, et al., Mitochondrial bioenergetics, mass, and morphology are altered in cells of the degenerating human annulus. J Orthop Res. 2013 August; 31(8):1270-5, 2013; each incorporated in its entirety by reference herein). Experimental evidence suggests that these apoptosis proteins can be down-regulated with free-radical scavengers or other methods to down-regulate mitochondrial pro-apoptotic processes. In certain embodiments, the use of focused and targeted infrared light could accomplish this goal. Research efforts to increase local production of neurotrophic factors (Natsume A, et al., Bcl-2 and GDNF delivered by HSV-mediated gene transfer after spinal root avulsion provide a synergistic effect. J Neurotrauma. 19(1):61-8, 2002; Lang E M, et al., Single-dose application of CNTF and BDNF improves remyelination of regenerating nerve fibers after C7 ventral root avulsion and replantation. J Neurotrauma. 25(4): 384-400, 2008; each incorporated in its entirety by reference herein) reflects the premise of neurotrophin deficiency within the spinal nerve roots (Obata K, et al., Expression of neurotrophic factors in the dorsal root ganglion in a rat model of lumbar disc herniation. Pain. 99(1-2): 121-32, 2002; incorporated in its entirety by reference herein). Invasive methods of increasing neurotrophins in the local environment of the damaged spinal nerve root has lead to improved recovery and function (Ramer M S, et al., Neurotrophin-3-mediated regeneration and recovery of proprioception following dorsal rhizotomy. Mol Cell Neurosci. 19(2):239-49, 2002; Wu W, Li L, et al., GDNF and BDNF alter the expression of neuronal NOS, c-Jun, and p75 and prevent motoneuron death following spinal root avulsion in adult rats. J Neurotrauma. 20(6):603-12, 2003; each incorporated in its entirety by reference herein). In certain embodiments, the present methods could regulate mitochondrial apoptotic proteins and increase neurotrophins in and around the nerve roots in a safe and non-invasive manner.

Photobiomodulation

In the past, a number of low level laser therapies have been developed that attempt to address one or more of the above issues. Near-infrared (NIR) light has been investigated for its ability to modulate intracellular reparative mechanisms. NIR can facilitate wound healing, promote muscle repair, and angiogenesis. The application of NIR by low-power laser or by light-emitting diode, referred to as either laser phototherapy or near-infrared photobiomodulation, has been studied and applied clinically in a wide array of ailments, including skin ulcers, osteoarthritis, peripheral nerve injury, low back pain, myocardial infarction, and stem cell induction. Since NIR passes relatively efficiently through bone, several studies of transcranial near-infrared light therapy (NILT) in animal models of brain damage have been conducted by multiple laboratories. A large clinical trial of NILT for acute stroke showed clinical improvement; however, a subsequent Phase III clinical trial failed to show benefit at an interim futility analysis. This and other findings of ineffective protocols for NIR in a variety of pathological conditions raise an important question about the necessary elements of an effective therapy Summary on Mechanism of Near-Infrared Photobiomodulation Current data indicates that near-infrared photons of wavelengths between 600-1,200 nm are critical to infrared phototherapy. These wavelengths are absorbed by cytochrome-c-oxidase in the mitochondrial respiratory chain which increases the activity of the respiratory chain and leads to an increase in adenosine triphosphate (ATP) production. Simply increasing ATP in wounded or underperfused cells may be sufficient to stimulate cells in areas of injury or metabolic derangement; however, tissue culture and animal studies implicate secondary molecular and cellular events. Near infrared light appears to alter nitric oxide levels, which may have downstream effects. NIR appears to modulate reactive oxygen and reactive nitrogen species. As a result of the primary events in the mitochondria there is increased energy in the cell. There is a resulting increased oxygenation and displacement of nitric oxide within the cell. Early response genes also are activated. Near-infrared light activates nuclear factor kappa B, which is a redox sensitive transcription factor. This pro-survival transcription factor modulates the expression of numerous genes, including ones involved in inflammation, early response, and cell survival. As a consequence of near-infrared phototherapy numerous genes in both the mitochondria and the cell nucleus are activated. There is increased transcription of over 100 genes. In particular, cell survival genes, and neural differentiation factors are transcribed. Increased synaptogenesis occurs. The production of numerous growth factors increases; and several inflammatory mediators are upregulated.

Mechanisms of Photobiomodulation

NIR light in the wavelength range of 600-1,200 nm has significant photobiomodulation capability. Current data most strongly support that absorption of NIR photons by cytochrome-c oxidase (COX) in the mitochondrial respiratory chain is the key initiating event in photobiomodulation. Irradiation of COX increases the activity of the entire electron transport chain producing more adenosine triphosphate (ATP). In addition, COX is auto-inducible and its gene expression is activity dependent, such that NIR irradiation may increase the amount of available COX over time. NIR's effect has been studied in isolated mitochondria preparations. Irradiation with 632 nm light results in increased proton electrochemical potential and increased ATP production. COX activity and oxygen consumption also increases. A more recent study confirmed increased oxygen consumption and showed increased activation of several electron transport chain components. In the setting of acute neurotrauma, this increase in energy supply may be sufficient to reduce the consequences of injury. Neurons are often forced into anaerobic metabolism, which results in acidosis, insufficient energy to maintain ion pumps, and calcium overload. Later in the sequence of events following neurotrauma, more energy is required than at baseline due to the large energy requirements of repair. Increasing ATP during acute neurotrauma alone may be sufficient, but NIR appears to initiate a number of other events in the mitochondria.

With NIR exposure, induction of mitochondrial RNA synthesis, as well as protein synthesis, occurs. More recent work has shown NIR induces the upregulation and downregulation of numerous genes both in the nucleus and in the mitochondria of various cell types. Apoptosis-inhibiting genes are upregulated (eg, Janus kinase binding protein). Meanwhile, apoptosis-promoting genes, such as heat shock 70 k Da protein 1A and caspase 6, are downregulated. Expression of genes for antioxidants and inhibitors of the effects of ROS are increased. Similar work in the retina has shown that genes involved in cell survival, antioxidant production, transcription, and growth factor production are also upregulated in neural retina cells.

Data from tissue culture and animal studies of NIR reveal an increase in growth factor expression and subsequent cell proliferation. Examples of these key growth factors include nerve growth factor, brain-derived neurotrophic factor, transforming growth factor-beta, and vascular endothelial growth factor, which may contribute to late brain remodeling after TBI. For example, a fivefold increase in nerve growth factor mRNA transcription occurred after irradiation of skeletal muscle cell culture with 633 nm NIR light.

Recent data suggest that transcranial NIR phototherapy can increase the process of neurogenesis in adult mice with stroke or TBI. Increased numbers of neuroprogenitor cells have been demonstrated in both the dentate gyrus of the hippocampus and in the subventricular zone of the lateral ventricle of mouse models. These cells also demonstrate increased expression of a microtubule protein associated with migrating neuroblasts. Some studies provide evidence that NIR phototherapy may increase the process of synaptogenesis. Together, these processes may aid in the neuroplasticity responsible for neural repair and improved function in cases of chronic TBI.

These cellular changes appear to persist for considerably longer than the interval of light application (when delivered at appropriate wavelengths and amplitudes). For example, low level (red and) near-infrared light therapy (LLLT) of a power density of 0.9-36 J/cm$^2$ applied in a single treatment at 24 hours post-stroke in animal models yielded a reduction in neurological deficits, as well as histochemical evidence of neuron proliferation and migration. A single application of LLLT in rodent models of TBI had similar benefits. Interestingly, these benefits were not immediately apparent. Rather, a delay of 1-4 weeks was noted, consistent with a progressive regeneration cascade set in motion by the NIR exposure.

Limitations of Current Photobiomodulation Protocols

Prior clinical applications of NIR photomodulation have utilized LLLT emitters and prolonged courses of daily treatments often extending over months (Naeser M A, et al., Improved cognitive function after transcranial, light-emitting diode treatments in chronic, traumatic brain injury: two case reports. *Photomed Laser Surg.* 29(5): 351-358, 2011; Nawashiro H, et al., Focal increase in cerebral blood flow after treatment with near-infrared light to the forehead in a patient in a persistent vegetative state. *Photomed Laser Surg.* 30(4):231-3; 2012; each incorporated in its entirety by reference herein). For example, the first published study of NIR therapy for TBI in humans described two cases of chronic mTBI with significant disability (Naeser et al., 2011). Each patient had marked neuropsychological improvement after a prolonged series of LLLT treatments using 870 and 633 nm light emitting diodes (LED) arrays over 4-72 months. Yet, some clinical and laboratory studies of LLLT have failed to consistently demonstrate benefit (Lavery L A, et al., Does anodyne light therapy improve peripheral neuropathy in diabetes? A double-blind, sham-controlled, randomized trial to evaluate monochromatic infrared photoenergy. *Diabetes Care.* 31(2):316-21, 2008; Giacci M K, et al. Differential effects of 670 and 830 nm red near infrared irradiation therapy: a comparative study of optic nerve injury, retinal degeneration, traumatic brain and spinal cord injury. *PLoS One.* 9(8):e104565, 2014; Kolari P J. Penetration of unfocused laser light into the skin. *Arch Dermatol Res.* 277(4):342-4, 1985; Franzen-Korzendorfer H, et al., The effect of monochromatic infrared energy on transcutaneous oxygen measurements and protective sensation: results of a controlled, double-blind, randomized clinical study. *Ostomy Wound Manage.* 2008; 54(6):16-31, 2008; each incorporated in its entirety by reference herein). For example, Lavery and colleagues (2008) demonstrated that LLLT (890 nm LED delivering 1.3 J/cm2 for 40 min daily for 90 days) did not yield significant improvement in nerve conduction velocity in patients with diabetic neuropathy. Similarly, treatment of a rat model of contusive spinal cord injury with LLLT (830 nm at 22.6 J/cm2 or 670 nm at 28.4 J/cm2) for 30 min per day for five days resulted in no significant functional improvement and no reduction in lesion size. The identical treatment regimen was applied to a rat model of TBI with no detectable improvement in motor or sensory function or change in lesion size (Giacci et al., 2014). In this animal model, they calculated 2.6 J/cm2 reached the spinal cord with each treatment. This is within the range of reported beneficial doses; yet, it was not effective. Note that several studies have shown that LLLT radiant energy is almost completely absorbed in the first 1 mm of skin (Esnouf A, et al., Depth of penetration of an 850 nm wavelength low level laser in human skin. *Acupunct Electrother Res.* 32(1-2):81-6, 2007; Bashkatov A N, et al., Optical properties of human skin, subcutaneous and mucous tissues in the wavelength range from 400 to 2000 nm. *J. Phys. D: Appl. Phys.* 38:2543-2555, 2005; each incorporated in its entirety by reference herein).

A clinical example of this discrepancy has unfolded in the clinical trials for the treatment of stroke utilized in the NEST-1 and NEST-2 trials (Zivin J A, et al. Effectiveness and safety of transcranial laser therapy for acute ischemic stroke. *Stroke.* 40(4):1359-64, 2009; Stemer A B, et al., The Evolution of Transcranial Laser Therapy for Acute Ischemic Stroke, Including a Pooled Analysis of NEST-1 and NEST-2. *Curr Cardiol Rep.* 12:29-33, 2010; each incorporated in its entirety by reference herein). Lapchak (Lapchak P A. Taking a light approach to treating acute ischemic stroke patients: Transcranial near-infrared laser therapy translational science. *Ann Med.* 2010; 42(8):576-86, 2010; incorporated in its entirety by reference herein) reported that the physical parameters of NILT in these studies may have delivered insufficient energy to cortical tissues to be effective. Therein, 808 nm NIR with energy densities of 0.9 J/cm2 was applied to the human scalp at multiple sites for a total of 40 minutes (Zivin et al., 2009; Stemer et al., 2010). Note that animal models of both stroke and TBI indicate NIR energy densities in the range of 0.9 J/cm2 to 36 J/cm2 yielded significant biochemical and behavioral changes (Monies et al., 2015; Henderson and Monies, 2015a; Chung H, et al., The nuts and bolts of low-level laser (light) therapy. *Ann Biomed Eng.* 40(2):516-33, 2012; Oron A, et al., Low-level laser therapy applied transcranially to mice following traumatic brain injury significantly reduces long-term neurological deficits. *J Neurotrauma.* 24:651-6, 2007; Oron A, et al., Low level laser therapy applied transcranially to rats after induction of stroke significantly reduces long-term neurological deficits. *Stroke.* 37:2620-4, 2006; Xuan W, et al., Transcranial low-level laser therapy improves neurological performance in traumatic brain injury in mice: effect of treatment repetition regimen. *PLoS One.* 8(1):e53454, 2013; Khuman J, et al., Low-level laser light therapy improves cognitive deficits and inhibits microglial activation after controlled cortical impact in mice. *J Neurotrauma.* 29:408-17, 2012; each incorporated in its entirety by reference herein). The concern raised from the NEST studies (Lapchak, 2010) is that current clinical trials using LLLT to treat TBI may yield negative or inaccurate efficacy data, not because of the incapacity of NIR to invoke a change, but due to a dose error. Doses that are effective when directly applied to a monolayer of cells or when penetrating 0.2 mm through the skull of a rodent and the 5 mm through the full thickness of the mouse brainmay be insufficient to penetrate to 20-30 mm into the human brain.

We have been utilizing relatively high power (10-30 W) lasers at the wavelengths of 810 and 980 nm in the clinic to treat TBI with positive results. Skin is the first tissue encountered in the clinical application of NIR phototherapy and represents a barrier to effective penetration due to several factors. Human skin has multiple layers and, therefore, multiple interfaces. Each interface is a surface for scatter. In addition, each layer has different inherent optical properties (Anderson R R, Parrish J A. The optics of human skin. J Invest Dermatol. 77(1):13-9, 1981; Lister T, et al., Optical properties of human skin. J Biomed Opt. 17(9): 90901-1, 2012; each incorporated in its entirety by reference herein). The epidermis, comprised in part of keratin, collagen, lipids, and melanin has high absorption in the ultraviolet range, but also absorbs light in the infrared range of 600-1100 nM (Anderson & Parrish, 1981). The dermis comprised in part of collagen, elastin and proteoglycans, is of variable thickness and penetration varies as a result. Scattering is a predominate property of dermis. The dermis is also dense with blood vessels and the hemoglobin-rich blood therein. While hemoglobin has absorption peaks at 450, 550, and 600 nM (Lister et al., 2012), it also absorbs photonic energy in the clinical NIR range of 800-1100 nm (Fitzgerald M, et al., Red/near-infrared irradiation therapy for treatment of central nervous system injuries and disorders. *Rev Neurosci.* 2013; 24(2):205-26, 2013; incorporated in its entirety by reference herein). The NIR absorption of hemoglobin depends upon its oxygenation status, with carboxyhemoglobin having greater NIR absorption. Altogether, NIR photonic energy must first overcome the hurdle of penetrating skin to have impact on deeper structures.

Extensive research has shown that fluence within the range of 0.9-15.0 $J/cm^2$ within the brain is most effective in activating the biological processes involved in reversing or mitigating the pathophysiological effects of TBI. The attenuation of NIR energy as it passes through tissue has been examined in computer simulations, animal tissue, and human tissue. NIR penetration to the human brain is subject to attenuation by multiple tissues (skin, skull, dura, blood, cerebrospinal fluid) and multiple interfaces which scatter, absorb, and reflect the NIR light to varying degrees. We have shown through the use of higher wattage NIR lasers that we can deliver fluence at therapeutic levels to the depths of the brain without tissue heating or damage. The protocols have been applied in our clinic with excellent clinical results and no side effects.

More than Mere Hypothesis

While others have hypothesized potential benefits of NIR light therapy, they have been unable to demonstrate actual clinical efficacy. For example, the NEST trials for stroke by deTaboada and others were ultimately determined to be ineffective. Similarly, uses of low level NIR for peripheral neuropathy and/or radiculopathy have been largely ineffective. In marked contrast to these hypothetical claims, we have definitively shown clinical improvement in patients with TBI utilizing high-power NIR light sources and have demonstrated conclusively in laboratory studies that NIR at these power levels reach the desired depths of tissue with sufficient fluence to exert a meaningful biological effect.

The science is now clear. Current low-level NIR treatments fail to penetrate to sufficient depths while retaining sufficient remaining energies. Our recent tissue studies demonstrate no penetration of low-level NIR energy through 2 mm of skin or 3 cm of skull and brain. Therefore Low Level Infrared Therapy is not effective for treatment of Neuro-Degenerative conditions. Furthermore, it does not penetrate down to the joints of muscular tissue in a high percentage of most sports related injuries, falls and other neuro-musculature conditions.

Conversely, our treatment methodologies, using medium-level 10.01-30.00 watt (continuous or pulsed), yields 0.45% to 2.9% of 810 nm light penetration through 3 cm of tissue. A 15 W 810 nm device NIR delivered 2.9% of the surface power density. Pulsing at 10 Hz and 50% duty cycle reduced the dose of light delivered to the surface by 50%, but 2.4% of the surface energy reached the depth of 3 cm. Approximately 1.22% of the energy of 980 nm light at 10-15 watts penetrated to 3 cm. These data are reviewed in the context of literature on low-power NIR penetration, wherein less than half of 1% of the surface energy could reach a depth of 1 cm. NIR in the power range of 10-15 watts at about 810 nm through about 980 nm can provide fluence within the range shown to be biologically beneficial at 3 cm depth. Insufficient energy has been utilized in transcranial infrared treatment protocols. This is a short-coming of previous work and patents in this field. We have demonstrated in our clinical studies and tissue penetration research, the increased penetration of medium-level NIR into these tissues, which results in dramatically improved therapeutic outcome in patients with Depression, Traumatic Brain Injury, Anxiety, and other neurological/psychiatric issues, including those related to neuro-degenerative diseases.

What are needed are novel treatment methodologies that can be utilized to treat TBI, IPD, ADSD, PTSD, DA, MS, SCI, PNL, RDL, STR, MTD and other diseases, conditions, and dysfunctions using medium-level NIR energies, in combination with pharmacological interventions, which together modulate mitochondrial function and upregulate neurotrophin production and activity.

Properties of Infrared Light

Light has fundamental physical properties which are relevant to its clinical use. Light is a form of electromagnetic radiation which has properties of both waves and particles. Light is characterized by its wavelength (distance between two peaks), frequency, and amplitude. Light is also characterized by its energy content. This energy is quantified as joules (J). The amount of energy delivered per unit time constitutes the power of light in watts (W=J/second). For medical applications, light is typically reported in terms of wavelength (nm), energy (J), irradiance or power density ($W/cm^2$), and radiant exposure or fluence or dose ($J/cm^2$).

NIR has a number of biological effects, but it is critical to understand the physical interactions between tissue and light. When light impinges on the surface, a portion (10%) is reflected Penetration of NIR through tissues is determined by several factors: wavelength, energy, attenuation coefficient (composed of scatter, refraction, and absorption), area of irradiance, coherence, and pulsing. In general, longer wavelengths (up to 1,000 nm) will penetrate deeper; however, the absorption of water begins to predominate above 1,000 nm. Increases in power density, in general, will lead to greater penetration. More photons will traverse the tissue. The area of surface irradiation also affects penetration due to scattering effects.

Pulsing of NIR also increases the depth of penetration and the amount of energy delivered to any given point at the peak of a pulse. Yet, pulsing allows for troughs of energy output such that the overall energy delivered to the tissue can be equivalent or even lower than that delivered by a continuous emission. Pulsing is a property of lasers which cannot be duplicated by LEDs.

SUMMARY

To date, we have been utilizing relatively high power (10-30 W) lasers at the wavelengths of 810 and 980 nm in clinic to treat TBI with positive results. NIR as employed in our novel treatment methodologies can also be used in the treatment of stroke, PTSD, depression, anxiety, IPD, dementia, AD, MS, and a variety of neuropathies, pain, among other disorders. Skin is the first tissue encountered in the clinical application of NIR phototherapy and represents a barrier to effective penetration due to several factors outlined in prior text.

One embodiment of a method of treatment is the non-invasive delivery of infrared light in wavelengths between 200-2000 nm at a surface wattage of between 0.01 to 50.00 watts. The duration of each treatment varies, in one embodiment from 30 seconds to 30 minutes, and can be conducted using a specific pulsed NIR technique for minimizing surface tissue heating. This is a novel process of non-invasive NIR/laser peripheral therapy and transcranial phototherapy. Prior applications were with very low levels of near infrared (NIR) therapy; most less than 1 watt with some up to 5 watts. The therapy we have been conducting and which is disclosed herein is with 10.1-30 watts. Embodiments of the methodologies can be practiced with a laser unit having a control for wavelength, wattage of 0.01-50 watts and a Hertz control. A pulsed (on and off laser beam) control for 1-1000 milliseconds may also be utilized. From our data, we estimate that in our clinical applications of high-powered NIR lasers, we are delivering 0.64-1.95 Joules per square cm to a depth of 30 mm. This is 100-fold greater fluence than that delivered by an LED system, but within the range of fluence shown to have beneficial biological effects. A hand held applicator with 1 cm aperture is used in one embodiment to produce approximately 0.64-1.95 Joules per square cm. A display detailing watts, Time, Continuous Wave or Pulsing, and Joules of therapy is useful. The utilized laser unit has FDA approval for use on humans, with safety training, and patient safety measures, eye protection and contraindications. A computer-controlled applicator is used in one embodiment.

By using our protocols, we are able to penetrate 3+ cm into the skin/skull/brain. Laboratory research has shown that infrared light can stimulate many brain processes, stimulate the mitochondria, increase ATP, alter nitric oxide (NO) levels, activate genes, increase nerve growth factors, increase synapse formation, and activate other processes.

Ketamine Infusion—Effects on Neurotrophins and Mitochondria

The dissociative anesthetic, ketamine, has found application in the treatment of non-responsive depression. In our embodiments including ketamine therapy, when we refer to ketamine therapy we are defining ketamine therapy to include the administration of ketamine, the most likely candidate molecule along with ketamine, the metabolite of ketamine (2R,6R)-hydroxynorketamine, and/or the class of drugs with which ketamine is associated.

Ketamine is an antagonist at the glutaminergic N-methyl-D-aspartate (NMDA) receptor. Studies of the mechanism of ketamine's action have revealed a surprising finding with application to numerous disorders. Essentially, ketamine activates the brain's and the body's intrinsic repair processes. Following the seminal study by Berman and colleagues (Berman R M, et al., 2000 Antidepressant effects of ketamine in depressed patients. Biol Psychiatry 15; 47(4): 351-4, 2000, incorporated in its entirety by reference herein), which showed that sub-anesthetic dose infusions of the dissociative anesthetic ketamine produced a rapid antidepressant response, additional studies of single infusions of ketamine confirmed this initial finding—ketamine at 0.5 mg/kg infused over a 30-40 minute period induces a rapid reduction in depressive symptoms and suicidal ideation in approximately 60-75% of patients (Berman R M et al., 2000; Zarate C A Jr, et al., A randomized trial of an N-methyl-D-aspartate antagonist in treatment-resistant major depression. Arch Gen Psychiatry 63(8):856-64, 2006; Price R B et al., Effects of intravenous ketamine on explicit and implicit measures of suicidality in treatment-resistant depression. Biol Psychiatry 66(5):522-6, 2009; each of which is incorporated in its entirety by reference herein). One limitation of ketamine was the symptom relief with single infusions typically lasted only 4-10 days. Multiple infusions were then explored (Shiroma P R et al., Augmentation of response and remission to serial intravenous subanesthetic ketamine in treatment resistant depression. J Affect Disord 155:123-9; 2014 incorporated in its entirety by reference herein), but actual clinical experience has revealed persistent changes in depression, suicidal ideation, anxiety, and PTSD with multiple infusions over time (Henderson T A, Practical Application of the Neuroregenerative Properties of Ketamine—Real World Treatment Experience, Neural Regeneration Research, 2016, incorporated in its entirety herein by reference). Since a major mechanism by which ketamine relieves depression, PTSD, and anxiety is by the activation of multiple pathways leading to the enhanced expression of BDNF, one embodiment would involve the use of this mechanism of upregulating BDNF to treat TBI, IPD, AD, MS, and other central and peripheral maladies. Based on the evidence from animal models, it is probable that long-lasting alterations in the neurons, dendrites, spines, and circuits occur with repeated ketamine infusions. One embodiment would utilize ketamine delivered orally. Another embodiment would utilize ketamine delivered intranasally. Another embodiment would utilize ketamine delivered intra-muscularly. Extensive clinical experience has shown that approximately 80% of patients treated with ketamine for depression see a favorable clinical response. This argues strongly in favor of a fundamental improvement in the neurotrophic environment and therefore the mitochondrial health of the neurons involved.

Possible Mechanisms of Action of Ketamine

The mechanisms underlying the antidepressant effects of ketamine are not simply due to glutamate receptor inhibition. Rather, ketamine binding to an NMDA receptor, if coupled to a mature α-amino-3-hydroxy-5-methul-4-isoxazole propionic acid (AMPA) receptor, activates eukaroyotic elongation factor 2 (eEF2) via a kinase. This, in turn, activates BDNF protein synthesis, particularly in neuronal dendrites (Browne and Lucki, Antidepressant effects of ketamine: mechanisms underlying fast-acting novel antidepressants. Front Pharmacol 27; 4:161; 2013; Monteggia L M et al., The role of eukaryotic elongation factor 2 kinase in rapid antidepressant action of ketamine Biol Psychiatry 73(12):1199-203; 2013; Bjorkholm and Monteggia, BDNF—a key transducer of antidepressant effects. Neuropharmacology 102:72-79; 2015 each of which is incorporated in its entirety by reference herein). The concomitant depolarization of AMPA receptors leads to calcium-dependent exocytosis of BDNF, which can then bind to postsynaptic trkB receptors (Browne and Lucki, 2013; Scheuing L et al., Antidepressant mechanism of ketamine perspective from preclinical studies. Front Neurosci 9:249; 2015 each of which is incorporated in its entirety by reference herein). TrkB receptors initiate numerous pathways, including early response genes and the mammalian target of rapamycin (mTOR) pathway which also leads to increased BDNF translation (Scheuing L et al., 2015; Duman R S, Pathophysiology of depression and innovative treatments: remodeling glutamatergic synaptic connections. Dialogues Clin Neurosci 16(1):11-27; 2014; each of which is incorporated in its entirety by reference herein). Moreover, BDNF has the ability to regulate mTOR and, thus, creates a positive feedback loop leading to further increase of BDNF production (Hoeffer and Klann, mTOR signaling: at the crossroads of plasticity, memory and disease. Trends Neurosci 33(2):67-75; 2010 incorporated in its entirety herein by reference). mTOR is localized in the dendrites and can rapidly initiate the translation of synaptic proteins and other mediators of neuroplasticity. Post-mortem studies of patients with depression have revealed decreased BDNF expression in the hippocampus (Dwivedi Y et al., Altered gene expression of brain-derived neurotrophic factor and receptor tyrosine kinase B in postmortem brain of suicide subjects. Arch Gen Psychiatry 60(8):804-15; 2003; Chen B et al., Increased hippocampal BDNF immunoreactivity in subjects treated with antidepressant medication. Biol Psychiatry 50(4):260-5; 2001; each of which is incorporated in its entirety by reference herein) and loss of neurons. Knockdown of BDNF levels in the hippocampus, in other words, genetically programmed brain injury, manifest depressive behaviors in mice (Taliaz D et al., Knockdown of brain-derived neurotrophic factor in specific brain sites precipitates behaviors associated with depression and reduces neurogenesis. Mol Psychiatry 15(1):80-92; 2010; incorporated in its entirety herein by reference). Rodent models of stress-induced depression, anxiety, PTSD, and neuronal loss also show decreased BDNF expression in the hippocampus, which can be reversed with ketamine (Browne and Lucki, 2013), over-expression of trkB (Koponen E et al., Overexpression of the full-length neurotrophin receptor trkB regulates the expression of plasticity-related genes in mouse brain. Brain Res Mol Brain Res 130(1-2):81-94; 2004; incorporated in its entirety herein by reference), or local micro-infusion of BDNF (Shirayama Y et al., Brain-derived neurotrophic factor produces antidepressant effects in behavioral models of depression. J Neurosci 22(8):3251-61; 2002; Gardier A M, Antidepressant activity: contribution of brain microdialysis in knock-out mice to the understanding of BDNF/5-HT transporter/5-HT autoreceptor interactions. Front Pharmacol 4:98; 2013; each of which is incorporated in its entirety herein by reference).

The inhibition of the ketamine's antidepressant effects has been explored by many laboratories. Blocking the AMPA receptor appears to prevent the effects of ketamine on animal models of depression (Zunszain P A et al., Ketamine synaptogenesis, immunomodulation and glycogen synthase kinase-3 as underlying mechanisms of its antidepressant properties. Mol Psychiatry 18(12):1236-41; 2013; incorporated in its entirety by reference herein). Blockade of mTOR with rapamycin pretreatment also prevents the antidepressant effects of ketamine in animal models (Li N et al., mTOR-dependent synapse formation underlies the rapid antidepressant effects of NMDA antagonists. Science 329 (5994):959-64; 2010; incorporated in its entirety herein by reference). Notably, trkB inhibition does not block the immediate benefits of ketamine upon depression, but does prevent the enduring effects (Browne and Lucki, 2013). These studies have been extensively reviewed elsewhere (Monteggia et al., 2013; Zunszain et al., 2013; Scheuing L et al., Antidepressant mechanism of ketamine perspective from preclinical studies. Front Neurosci 9:249; 2015; each of which is incorporated in its entirety herein by reference). A tyrosine kinase inhibitor, which prevents the autophosphorylation of trkB, prevented the sustained antidepressant effect of ketamine (as measured at one week in an animal model), but only if administered prior to the ketamine (Carreno F R et al, Activation of a ventral hippocampus-medial prefrontal cortex pathway is both necessary and sufficient for an antidepressant response to ketamine Mol Psychiatry doi: 10.1038/mp.2015.176; 2015; incorporated in its entirety by reference herein). Furthermore, this sustained antidepressant response could be prevented by administering lidocaine to the ventral hippocampus immediately prior to administering ketamine systemically (Carreno et al., 2015). Notably, neither transient silencing of neuronal impulse activity in the ventral hippocampus nor inhibiting auto-phosphorylation of the trkB receptor prevented the immediate antidepressant benefit of ketamine in this animal model, but either eliminated the sustained effect—in other words, these maneuvers prevented the upregulation of BDNF which is essential to the prolonged antidepressant effect, as well as to the reparative effects elucidated herein for other conditions.

Taken together, data and the medical literature (e.g., Henderson 2016) posit that ketamine has both immediate and delayed effects. The immediate effects include: presynaptic disinhibition of glutamatergic neurons, creating a glutamate surge; increased activation of the AMPA receptor in conjunction with inhibition of NMDAR; inhibition of GSK-3, and synaptogenesis and synaptic potentiation resulting from translation of BDNF and activation of the mTOR pathway. The delayed effects of ketamine likely include: activation of eEF2 leading to BDNF translation; enhanced synaptic connectivity; neurogenesis; dendritic arborization; and immunomodulation. Neuronal activity (as well as trkB auto-phosphorylation) in the ventral hippocampus is required for the delayed effects of ketamine to occur. The delayed effects potentially underlie persistent neurotrophin upregulation, neuroplasticity and persistent antidepressant effects. These neuroplasticity effects in some embodiments could be reparative for TBI, stroke, IPD, MS, dementia, AD, depression, anxiety, and various neuropathies/radiculopathies, among other disorders. These mechanisms may also underlie the neuroregenerative properties of near-infrared light, which also activates BDNF and has immunomodulatory effects (Monies L D M et al., Treatments for traumatic brain injury with emphasis on transcranial near-infrared laser phototherapy. Neuropsychiatr Dis Treat 20; 11:2159-75. doi: 10.2147/NDT.S65809; 2015; incorporated in its entirety herein by reference).

Administration of Ketamine to Potentiate BDNF and Mitochondrial Function

Ketamine is a dissociative anesthetic which can be administered orally, intranasally, intramuscularly, and intravenously. The best absorption and bioavailability occurs with intravenous administration. In addition, intravenous administration lowers the risk of untoward adverse events related to dose or levels of metabolites (Henderson, 2016). In certain embodiments, ketamine can be administered intravenously over a period of time—ranging from 20-90 minutes. In certain embodiments, ketamine can be administered over longer periods of time—ranging from 1-48 hours. The longer the duration of time in which ketamine is in contact with the NMDA receptor, the more robustly BDNF is upregulatedA typical embodiment of ketamine administration by intravenous infusion involves screening the patient for contraindications to ketamine, reviewing the main effects, side effects, risks and benefits of ketamine administration, preparing the patient with instructions to be without food or drink for 6 hours prior to ketamine administration, and assuring that they have safe transportation after said infusion. At the time of the infusion, the patient would be monitored for blood pressure, ECG, and pulse oxymetry, preferably with an automatic sphygmomanometer and a visual monitoring system. Preferably, the patient would be monitored by a nurse anesthetist or anesthesiologist and placement of the intravenous line would be performed by medical professionals of this same level of expertise. Preferably, a crash cart, oxygen, and defibrillator would be available if needed. Ketamine would be delivered intravenously by a slow infusion. Ideally, an infusion pump would be used to assure the rate, consistency, and duration of the infusion. Dosing of the ketamine would be based upon ideal body weight. Dose of ketamine could range from 0.25-5 mg/kg over the course of 20-90 minutes. In certain embodiments, doses of 0.25-5.0 mg/kg could be delivered over the course of 1-48 hours. Following the infusion, the patient would be given adequate time to recover from the effects of ketamine After a minimum of 30 minutes, the patient would be allowed to leave the treatment facility, accompanied by a companion or family member who would provide transportation home. In other embodiments, ketamine would be administered intra-muscularly with monitoring afterwards, orally with a frequency of daily or greater, or intranasally with a frequency of daily or greater. In other embodiments, ketamine could be administered intermittently either orally, intra-muscularly, or intranasally. While a single infusion undoubtedly initiates upregulation of neurotrophins and modulation of mitochondrial dysfunction, multiple infusions, in most embodiments, are required to maximize the benefit to the patient. Given the fact that BDNF and other neurotrophins require several days to weeks to fully influence the underlying neurobiology (e.g., dendritic arborization, synaptogenesis, neurogenesis, etc.), the timing of repeat ketamine infusions likely should not be less than every 3 days. In certain embodiments, ketamine infusions on a weekly basis, or less frequent, have proven highly beneficial for depression, anxiety, PTSD, and other disorders. In certain embodiments, ketamine infusions separated by 2-20 weeks have provided symptom relief. In other embodiments, ketamine could be administered intermittently either orally, intra-muscularly, or intranasally. The actual timing of ketamine administrations for a particular patient, as well as the total number of administrations provided, is best decided on an individual basis. The individualized care enhances the neurobiological benefit for a particular patient, while minimizing costs for care (Henderson, 2016).

Quantitative Imaging and/or Quantitative Conduction Studies for Targeting a Focused Therapy and Monitoring Progression of Therapeutic Response The nature of one component of the claim is a focused beam of infrared light. In certain manifestations, accurate targeting of this focused beam of infrared light would improve the clinical outcome, regardless of the medical condition being treated. Targeting can be achieved in some instances with nerve conduction studies, which when performed in a quantitative fashion, provide accurate information concerning the specific nerves involved, their location within the body, the mapped distribution of nerve fibers, their relationship to a given spinal cord level, and their level of functioning (or health). Similarly, targeting areas of dysfunction within the brain requires accurate functional neuroimaging methods of visualizing the location and physical parameters of the area of dysfunction, as well as the level of functioning within the specific area of brain involved. Ideally, such a method should be non-invasive.

Once an area requiring treatment is localized, then a targeted focal therapy can be applied. Subsequently, the key issue will be to monitor the condition of the targeted tissue to determine if focal therapy is improving the condition of said tissue and to what extent. Both of these considerations will require the ability to assess the physiological or functional state of the tissue as well as quantitatively analyze any relative change from the baseline state. In certain embodiments, serial quantitative nerve conduction studies and serial quantitative functional neuroimaging can fulfill the requirements for both targeting and monitoring progression of therapeutic response.

Neuroimaging as a Tool for Targeting a Focused Therapy

Medical imaging is an invaluable tool in treating disease and dysfunction. Many types of imaging are known, and some can be used to produce useful images of the brain. These are known as neuroimaging. In certain embodiments, neuroimaging can provide vital spatial information about the area of brain injury or brain disease, such as location, depth, volume, positioning relative to other tissues, etc. Only functional neuroimaging modalities can provide information about the brain's physiological state and relative change in physiological state in response to a therapeutic intervention.

Overview of SPECT

SPECT is the most widely available technology for measuring brain function (Devous M D. SPECT functional brain imaging. In: Toga A W, Mazziotta J C, editors. Brain Mapping: The Methods, $2^{nd}$ ed. London: Academic Press: 2002:513-536; Devous M D. SPECT functional brain imaging: instrumentation, radiopharmaceuticals and technical factors. In: Van Heertum R L, Tikofsky R S, Ichise M, editors. Functional Cerebral SPECT and PET Imaging, 4th ed. Philadelphia: Lippincott Williams & Wilkins; 2010: 3-22; each incorporated in its entirety by reference herein). SPECT facilities outnumber PET facilities 12-fold. Using currently available radiopharmaceuticals, perfusion SPECT accurately represents regional cerebral blood flow (rCBF). rCBF is a valid marker for neuronal activity over most of the physiological range of cerebral blood flow, because under most circumstances rCBF is tightly coupled to neuronal metabolism. This principle underlies SPECT perfusion imaging and functional magnetic resonance imaging. In certain embodiments, SPECT can be a powerful tool for localizing brain dysfunction and for monitoring/documenting quantitative changes in said dysfunction.

SPECT was first measured with Xenon (133Xe), an inert gas that precisely quantifies cerebral blood flow. Commonly used radiopharmaceuticals currently include 99mTc-hexamethylpropylene amine oxime (HMPAO), 99mTc-ethylcysteinate dimer (ECD), and N-isopropyl-p-23Iodoamphetamine (IMP). All of the currently available tracers closely follow 133Xe-derived rCBF values over the physiological range. HMPAO has many advantages, including but not limited to low risk of allergic reaction, higher extraction, and better signal-to-noise ratio. 125I-IMP is widely used outside the United States with excellent results. Of note, the radiopharmaceuticals for SPECT perfusion imaging are widely available and approved by federal pharmaceutical regulatory agencies.

SPECT for the Diagnosis, Localization, and Characterization of TBI

Traditional brain imaging modalities such as magnetic resonance imaging (MRI) and computed tomography (CT) provide little evidence in cases of mild-to-moderate TBI. This is likely secondary to the fact that CT and MRI detect structural defects, which in the case of mild-to-moderate TBI are likely either not present or below the imaging resolution of MRI or CT. CT and MRI certainly have their applications in helping to diagnose traumatic brain injuries (especially severe injuries). Typically, CT remains a vital first step in the assessment of any TBI due to its superior capacity to visualize hemorrhage and skull fracture. Unfortunately, the sensitivity of CT is very low for mild-to-moderate TBI. CT scans can be useful for screening for intracranial hemorrhage or skull fracture, but it offers little information on the brain parenchyma. The majority of CT scans in mild-to-moderate TBI are normal. A significant body of literature shows that SPECT scans are more sensitive for mild to moderate TBI than CT scans. In a combined sample of over 4,000 mild TBI cases, roughly 5-10% had abnormal CT scans. These positive cases were most likely to be associated with headache, vomiting, increased age, alcohol or drug intoxication, anterograde amnesia, head or neck lacerations, or seizures (Borczuk P. Predictors of intracranial injury in patients with mild head trauma. Ann Emerg Med. 25(6):731-6; 1995; Miller E C, et al., Utilizing clinical factors to reduce head CT scan ordering for minor head trauma patients. J Emerg Med.15(4):453-7; 1997; Haydel M J, et al., Indications for computed tomography in patients with minor head injury. N Engl J Med. 2000 Jul. 13; 343(2):100-5, 2000; each incorporated in its entirely herein by reference). In a prospective study of 92 adult and child patients with TBI compared to normal database of 40 subjects, SPECT scans and CT scans were performed within 72 hours of injury (Gowda N K, et al., Technetium Tc-99m ethyl cysteinate dimer brain single-photon emission CT in mild traumatic brain injury: a prospective study. AJNR Am J Neuroradiol. 27(2):447-51, 2006; incorporated in its entirely by reference herein). The CT scans were abnormal in only 34% of cases. In contrast, the SPECT scans were abnormal in 63% of cases. In all cases with positive SPECT scans, the findings were colocalized with lesions revealed on CT scan.

Moreover, SPECT scans have also proven to be more sensitive for detecting mild-to-moderate TBI than anatomical MRI scans. Indeed, in a retrospective study of 228 cases, SPECT revealed evidence of functional brain deficits in 68% of the cases, while CT scans and MRI scans were completely negative (Abu-Judeh H H, et al., SPECT brain perfusion findings in mild or moderate traumatic brain injury. JALASBIMN, 2(6), 2000. epub; incorporated in its entirety by reference herein). The SPECT scans revealed that 46% of cases had frontal lobe hypoperfusion, 55% had basal ganglia/thalamic hypoperfusion, and 18% had temporal lobe hypoperfusion.

The use of SPECT has been a topic of debate in the past. Currently, The Society of Nuclear Medicine (Juni J E et al., Society for Nuclear Medicine. Procedure guideline for brain perfusion SPECT using (99m)Tc radiopharmaceuticals 3.0. *J Nucl Med Technol.* 37(3):191-195, 2009; incorporated herein in its entirety by reference) and the European Association of Nuclear Medicine (Tatsch K, et al; European Association of Nuclear Medicine. European Association of Nuclear Medicine procedure guidelines for brain perfusion SPET using (99m)Tc-labelled radiopharmaceuticals. *Eur J Nucl Med Mol Imaging.* 29(10):BP36-P42, 2002; incorporated herein in its entirety by reference) recognize SPECT as having diagnostic and prognostic value for TBI (i.e. both in acute concussion and long-standing injury). The American College of Radiology (American College of Radiology. ACR-SPR practice parameter for the performance of single photon emission computed tomography (SPECT) brain perfusion and for brain death examinations. 2014; incorporated herein in its entirety by reference) cites symptomatic TBI, especially in the absence of CT and or MRI findings, as a clinical indication for the use of SPECT. It should be noted that the outdated 1996 TTASAAN report (No authors listed. Assessment of brain SPECT: report of the Therapeutics and Technology Assessment Subcommittee of the American Academy of Neurology. *Neurology.* 1996; 46(1):278-285.1996; incorporated herein in its entirety by reference) by the American Academy of Neurology, which concluded that SPECT was an experimental technique, was based on only six early studies—none of which are among the much more conclusive studies cited above. Its conclusions have been superseded by the more current literature.

To summarize the state of the current literature, a total of 903 patients included in 19 longitudinal studies demonstrated Level II A evidence for the utility of SPECT to identify lesions in the clinical setting of TBI. Of the 19 longitudinal studies, 14 (77%) had neurological or neuropsychology outcome measures to which SPECT abnormalities were correlated. A total of 2,121 patients in 52 cross-sectional studies of TBI were also reviewed. Areas most commonly injured in TBI are the frontal lobe (94%) and the temporal lobe (77%) of studies. These data are reviewed in detail in Raji and colleagues (Raji C A, et al. 2014).

Lesion Localization as a Key First Step to Treatment

Lesion location is a critical first step prior to administration of a laser-based treatment. Laser light is highly coherent and focused. As a result, it must be aimed at the area to be treated. SPECT has been repeatedly demonstrated to be superior to CT in localizing functional cerebral damage in TBI (Abdel-Dayem, H M, et al. SPECT brain perfusion abnormalities in mild and moderate traumatic brain injury. *Clincial Nuclear Medicine,* 23, 309-317, 1998; Nedd, K et al., 99mTc-HMPAO SPECT of the brain in mild to moderate traumatic brain injury patients: Compared with CT-A prospective study. *Brain Injury,* 7, 460-479, 1993; Bavetta, S, et al., A prospective study comparing SPET with MRI and CT as prognostic indicators following severe closed head injury. *Nucl Med Commun,* 15(12), 961-8, 1994; Ichise, M., et al., Technetium-99m-HMPAO SPECT, CT and MRI in the evaluation of patients with chronic traumatic brain injury: A correlation with neuropsychological performance. *Journal of Nuclear Medicine,* 34, 217-226, 1994; Cihiangiroglu, M, et al., Brain injury: Analysis of imaging modalities. *Neurological Research,* 24, 7-18, 2002; Newberg, A B, and Alavi, A. Neuroimaging in patients with head injury. *Seminars in Nuclear Medicine,* 33, 136-147, 2003; Gray, B. G., et al., Technetium-99m-HMPAO SPECT in the evaluation of patients with a remote history of traumatic brain injury: A comparison with x-ray computed tomography. *The Journal of Nuclear Medicine.* 33, 52-58, 192; each incorporated herein in its entirely by reference).

SPECT has also been repeatedly demonstrated to be superior to MRI in localizing functional cerebral damage in traumatic brain injury (Abdel-Dayem et al., 1998; Ichise et al., 1994; Prayer, L, et al., Cranial MR imaging and cerebral 99m Tc HM-PAO-SPECT in patients with subacute or chronic severe closed head injury and normal CT examinations. *Acta Radiologica,* 34, 593-599, 1993; Jacobs, A et al. Prospective Evaluation of Technetium-99m-HMPAO SPECT in Mild and Moderate Traumatic Brain Injury. *J Nucl Med.* 35(6); 947-8, 1994; Jacobs, A et al., One-year follow-up of Technitium-99m-HMPAO SPECT in mild head injury. *The Journal of Nuclear Medicine,* 37, 1605-1609, 1996; each incorporated in its entirely by reference herein).

SPECT in Monitoring Treatment Response and Recovery Progression

SPECT with its ability to detect TBI lesions better than other imaging modalities, such as MRI and CT, would in certain embodiments provide greater information in predicting outcome and enable planning for treatment and return to work issues accordingly. As the opportunity for healing the damage of brain injury improves as seen in certain embodiments of the current claim, the role of SPECT brain imaging to help evaluate progress in treatment and the possible need for additional treatment cannot be overemphasized.

SPECT has been found to have high predictive value at 3, 6 and 12 months post injury of 90%, 100% and 100%, respectively (Jacobs et al., 1996). Thus, it is clear that patients with persistent clinical symptoms continue to have abnormal follow-up SPECT findings. As with any abnormality, the ability to determine progress over time is crucial in choosing the best treatment option. As such, continued abnormal SPECT findings during a certain course of rehabilitation could indicate a treatment failure and a need for a different treatment approach.

SPECT brain imaging also has a proven high degree of negative predictive value—93% at 3 months and 100% at 12 months (Jacobs et al., 1996). Thus, a negative initial SPECT study completed within one week of head injury is a reliable indicator of a favorable clinical outcome. This capability can provide an initial screening tool for all TBI cases, giving a high level of confidence in making decisions about TBI cases with negative SPECT findings (Jacobs et al., 1996; Davalos, D. B., Bennett, T. L. (2002). A Review of the Use of Single-Photon Emission Computerized Tomography as a Diagnostic Tool in Mild Traumatic Brain Injury. *Applied Neuropsychology*, 9(2), 92-105, 2002; each incorporated in its entirety by reference herein).

SPECT in the Diagnosis, Differential Diagnosis, and Documenting Progression of Other Disorders In addition to TBI, SPECT has been shown to be superior to MRI in demonstrating other types of brain injury in a wide variety of conditions, including toxic encephalopathy (Callender T J et al.; Three-dimensional brain metabolic imaging in patients with toxic encephalopathy; *Environ Res*; 60(2); 295-319, 1993; Chiu N Y et al., Technetium-99m-HMPAO brain SPECT in neonates with hypoglycemic encephalopathy; *J Nucl Med*; 39(10); 1711-3, 1998; Celik Y et al. Brain SPECT findings in Wernicke's encephalopathy; *Neurol Sci*; 25(1); 23-6, 2004; each incorporated in its entirety by reference herein), systemic lupus erythematosis (Handa R et al., In vivo proton magnetic resonance spectroscopy (MRS) and single photon emission computed tomography (SPECT) in systemic lupus erythematosus (SLE); *Magn Reson Imaging; November*; 21(9); 1033-7, 2003; Oku K et al., Cerebral imaging by magnetic resonance imaging and single photon emission computed tomography in systemic lupus erythematosus with central nervous system involvement; *Rheumatology (Oxford)*; 42(6); 773-7, 203; each incorporated in its entirety by reference herein), Alzheimer's disease (Henderson, TA. The diagnosis and evaluation of dementia and mild cognitive impairment with emphasis on SPECT perfusion neuroimaging. CNS Spectrums, 17(4):176-206, 2012; incorporated in its entirety by reference herein), mild cognitive impairment (Henderson, T A. 2012), Parkinson's disease and related disorders (Van Laere, K, et al., Dual-Tracer dopamine transporter and perfusion SPECT in differential diagnosis of Parkinsonism using template-based discriminant analysis. J Nucl Med, 47:384-392, 2006; incorporated in its entirety herein by reference), PTSD (Amen, D G et al., Functional Neuroimaging Distinguishes PTSD from TBI in Focused and Large Community Datasets. *PLoS One*. 10(7): e0129659, 2015; Raji C A, Functional Neuroimaging with Default Mode Network Regions Distinguishes PTSD from TBI in a Military Veteran Population. *Brain Imaging Behav*. 9(3):527-34, 2015, each incorporated in its entirety herein by reference), depression (Willeumier K, et al., Decreased cerebral blood flow in the limbic and prefrontal cortex using SPECT imaging in a cohort of completed suicides. Transl Psychiatry. 1:e28, 2011; Chi K F, et al., Imaging predictors of remission to anti-depressant medications in major depressive disorder. J Affect Disord. 186:134-44, 2015; each incorporated in its entirety by reference herein), and stroke (Masdeu J C, and Brass L M. SPECT imaging of stroke. J Neuroimaging. 5 Suppl 1:S14-22, 1995; Hoggard N, et al., The imaging of ischaemic stroke. Clin Radiol. 2001 March; 56(3):171-83; 2001; each incorporated in its entirety by reference herein).

SPECT in Alzheimer's Disease and Dementias

Since its earliest use in dementia, SPECT imaging has undergone significant advancement in image acquisition and processing. Perhaps the earliest study (Bonte F J, et al., SPECT study of regional cerebral blood flow in Alzheimer disease. *J Comput Assist Tomogr.* 10(4):579-83, 1986; incorporated in its entirety by reference herein), documented decreased temporal lobe perfusion in 37 patients with AD using 133Xe perfusion SPECT. Early studies depended on visual subjective interpretation or "eyeballing." Inter-rater reliability was a significant factor. Early attempts at semi-quantitative analysis remained subjective and compromised.

When the entire extent of SPECT neuroimaging literature on the topic of dementia was examined and grouped based on camera type and comparator group (FTD, VaD, DLB, MCI, healthy elderly control), a somewhat different picture emerges. When differentiating AD from healthy elderly controls, studies using relatively low-resolution, single-headed gamma cameras yielded an overall sensitivity of 84% and an overall specificity of 83% (Henderson, T A., 2012). Studies utilizing multiheaded gamma cameras and often quantitative analysis yielded a modest, but clinically significant, increase in overall sensitivity from 84-89% and in overall specificity from 83-89% (Henderson, 2012). Longitudinal clinical studies have examined the sensitivity and specificity of baseline SPECT perfusion scans for the eventual diagnosis of AD. Hanyu and colleagues (Hanyu H, et al. Diagnostic accuracy of single photon emission computed tomography in Alzheimer's disease. Gerontology. 1993; 39(5):260-6, 1993; incorporated in its entirety by reference herein) examined a group of 219 patients and were able to distinguish 56 cases that would progress to AD based on decreased perfusion of the temporal and parietal lobes (sensitivity 82%, specificity 89%). As part of the Oxford Study to Investigate Memory and Aging, Jobst et al. followed 200 patients with dementia and 119 controls over 7 years. Seventy patients were autopsied, and baseline clinical evaluation alone yielded a sensitivity of 93% and a specificity of 46%, while baseline SPECT scans combined with clinical diagnosis did not change sensitivity, but increased specificity to 84% (Jobst K A, et al., Accurate prediction of histologically confirmed Alzheimer's disease and the differential diagnosis of dementia: the use of NINCDS-ADRDA and DSM-III-R criteria, SPECT, X-ray CT, and Apo E4 in medial temporal lobe dementias. Oxford Project to Investigate Memory and Aging. Int Psychogeriatr. 10(3):271-302, 1998; incorporated in its entirety by reference herein). Taken together, studies of perfusion SPECT in the diagnosis of AD with comparison to a longitudinal clinical course and/or histopathology demonstrate sensitivity in the range of 82-96% and a specificity in the range of 83-89%.

SPECT neuroimaging can be extremely helpful in the evaluation of dementia of a vascular origin. VaD can show widely varying regional blood flow patterns, reflecting its variable vascular source. As such, there is not a single characteristic pattern of perfusion or metabolic activity that identifies VaD dementia. FTD can be characterized on functional brain imaging by decreased function and associated hypoperfusion in the frontal lobes, caudate nuclei, and anterior temporal lobes (Henderson, 2012; Silverman D H. Brain $^{18}$F-FDG PET in the diagnosis of neurodegenerative dementias: comparison with perfusion SPECT and with clinical evaluations lacking nuclear imaging. J Nucl Med 2004; 45(4):594-607; 2004; Camargo E E. Brain SPECT in neurology and psychiatry. J Nucl Med 2001; 42(4):611-623, 2001; Talbot P R, et al. A clinical role for 99mTc-HMPAO SPECT in the investigation for dementia? J Neurol Neurosurg Psychiatry. 64(3):306-13, 1998; each incorporated in its entirety herein by reference). Hypoperfusion also can be found in the anterior cingulate gyms. In FTD, perfusion is generally spared in the posterior cingulate gyrus/precuneus (Henderson 2012). Based on correlation to autopsy data, posterior cingulate perfusion has a positive predictive value of 93% and a negative predictive value of 81% (Bonte F J, et al. Tc-99m HMPAO SPECT in the differential diagnosis of the dementias with histopathologic confirmation. Clin Nucl Med. 2006; 31(7):376-8, 2006; incorporated in its entirety by reference herein). Observations by a number of investigators using the modalities of PET, SPECT, and MRI support the validity of decreased posterior cingulate gyrus function as a diagnostic marker for AD that differentiates it from FTD (Henderson, 2012).

Idiopathic Parkinson's Disease and Other Parkinsonian Syndromes

Perfusion SPECT distinguishes IPD from other Parkinsonian syndromes, such as MSA or PSP. Specifically, in IPD, regional perfusion (or glucose metabolic) studies typically demonstrate a pattern of striatal and thalamic increased perfusion or metabolism contrasting with relative hypoperfusion/hypometabolism of the lateral parietal cortices and the motor cortices (Markus H S, et al., HMPAO SPECT in Parkinson's disease before and after levodopa: correlation with dopaminergic responsiveness. J Neurol Neurosurg Psychiatry, 57:180-185, 1994; Antonini A, et al., Brain flow changes before and after deep brain stimulation of the subthalamic nucleus in parkinson's disease. Neurol Sci, 2003; 24:151-152, 2003; Firbank M J, et al., Regional cerebral blood flow in Parkinson's disease with and without dementia. Neuroimage, 20:1309-1319, 2003; Van Laere, K, et al., Dopamine transporter SPECT using fast kinetic ligands: 123I-FP-beta-CIT versus 99mTc-TRODAT-1. Eur J Nucl Med Mol Imaging, 2004; 31:1119-1127, 2004; Eichelberg D, et al., The metabolic topography of parkinsonism. J Cereb Blood Flow Metab, 14:783-801, 1994; each incorporated in its entirety herein by reference). Increased striatal perfusion has been repeatedly demonstrated in IPD (Tachibana H, et al., Twelve month follow-up study of regional cerebral blood flow in Parkinson's disease. Dementia, 6:89-93, 1995; Firbank M J, et al., Longitudinal study of cerebral blood flow SPECT in Parkinson's disease wth dementia, and dementia with Lewy bodies. Int J Geriatr Psychiatry, 20:776-782, 2005; Imon Y, et al., SPECT image analysis using statistical parametric mapping in patients with Parkinson's disease. J Nucl Med, 40:1583-1589, 1999; Feigin A, et al., Tc-99m ethylene cysteinate dimmer SPECT in the diffrerential diagnosis of parkinsonism. Mov Disord, 2002; 17:1265-1270, 2002; each incorporated in its entirety by reference herein); indeed, a progressive increase in striatal perfusion has been correlated with increasing symptom severity in two longitudinal studies (Tachibana et al., '95; Firbank et al., '05). In contrast, metabolism (activity) is significantly decreased in patients with MSA (Ghaemi M. et al., Differentiating multiple system atrophy from Parkinson's disease: contribution of striatal and midbrain MRI volumetry and multi-tracer PET imaging. J Neurol Neurosurg Psychiatry, 2002; 73:517-523, 2002; Juh, R, et al., Different metabolic patterns analysis of Parkinsonism on the $^{18}$F-FDG PET. Eur J Radiol, 2004; 51:223-33, 2004; each incorporated in its entirety by reference herein). A correlation between striatal perfusion (or glucose metabolism) changes and progression of the disease symptoms has been recognized (Kuhl D E, et al., Patterns of local cerebral glucose utilization determination in Parkinson's disease by the F18-fluorodeoxyglucose method. Ann Neurol, 1984; 15:419-424, 1984; Piert M, et al., Determination of regional rate constants from dynamic FDG PET studies in Parkinson's disease. J Nucl Med, 1996; 37:1115-1122, 1996; Firbank et al. '05; each incorporated in its entirety by reference herein).

A series of studies have examined the diagnostic utility of a combined tracer approach to characterizing both dopaminergic integrity and perfusion (metabolism). van Laere and colleagues reported the largest and most statistically rigorous study utilizing dual-tracer imaging. With a combination of $^{99m}$Tc-ECD and $^{125}$I-FP-CIT, they examined the differences between a total of 129 patients with either IPD, essential tremor, MSA, PSP, and dementia with Lewy bodies over an average of 5.5 years (van Laere et al., '06). This study is distinct due to its large IPD sample size (N=58) and large MSA sample size (N=24). Patients with MSA showed a statistically significant decrease in perfusion in the bilateral posterior putamen and cerebellar vermis and hemispheres relative to patients with either IPD or essential tremor. Patients with PSP demonstrated decreased perfusion in multiple areas, including left frontal lobe, left caudate, anterior cingulate, and thalamus relative to IPD. Patients with IPD demonstrated significantly increased perfusion of the cerebellum relative to essential tremor, MSA, PSP, and dementia with Lewy bodies. Discriminant analysis revealed that essential tremor could be distinguished from the degenerative Parkinsonian diseases by DAT labeling in 93% of cases. The combination of DAT labeling and regional perfusion differences increased the discriminatory power to 97% of cases (van Laere et al., '06). Differentiating between the diseases was somewhat more challenging. DAT labeling could only distinguish IPD, MSA, and PSP in 58% of cases. Perfusion imaging could separate 68% of cases. However, the combination of the two techniques increased classification accuracy or differentiation of the degenerative diseases to 99% (van Laere et al., '06).

Post-Traumatic Stress Disorder

Perfusion SPECT also has been investigated in the evaluation of PTSD. For example, increased perfusion of the caudate has been associated with PTSD (Sachinvala N, et al., Increased regional cerebral perfusion by 99mTc hexamethyl propylene amine oxime single photon emission computed tomography in post-traumatic stress disorder. Mil Med. 165(6):473-9, 2000; incorporated in its entirety by reference herein). A small study using both perfusion SPECT and FDG PET showed that women with PTSD had significant decreases in perfusion in the left hippocampus and in the basal ganglia, and lower cerebral glucose metabolism in the left hippocampus and the superior temporal and precentral gyri than in the control group (Kim S Y, et al., Resting cerebral glucose metabolism and perfusion patterns in women with posttraumatic stress disorder related to sexual assault. Psychiatry Res. 201(3):214-7, 2012; incorporated in its entirety by reference herein). Another SPECT study showed that compared to controls, PTSD patients had increased cerebral blood flow in the limbic regions along with decreased perfusion in the superior frontal, parietal, and temporal regions (Chung Y A, et al. Alterations in cerebral perfusion in posttraumatic stress disorder patients without re-exposure to accident-related stimuli. Clinical neurophysiology: official journal of the International Federation of Clin Neurophysiol. 117(3):637-42, 2006; incorporated in its entirety by reference herein).

Raji and colleagues (Amen D G, et al., 2015; Raji C A, et al. 2015) analyzed over 20,000 SPECT scans of patients with TBI and/or PTSD compared to controls and found that quantitative analysis of the default-mode network allowed a high level of discrimination between the different states— with over 94% accuracy. Specifically, the DMN is hyperperfused in individuals diagnosed with PTSD and hypoperfused in patients diagnosed with TBI. The data suggests that a specific neural network, the DMN, is implicated in both PTSD and TBI contributing to the similarity in symptoms. In certain embodiments, SPECT may therefore allow clinicians to differentially diagnose PTSD and TBI. SPECT is capable of diagnosing PTSD using standard visual reads (Sachinvala et al., 2000; our personal experience) and using quantitative analysis (Raji et al., 2015).

Detection of Neurological Changes Using SPECT

We have utilized SPECT combined with quantitative analysis as a method to detect changes in neurological functions in a patient who had undergone infrared light treatment (Henderson T A & Monies L D, SPECT Perfusion Imaging Demonstrates Improvement of Traumatic Brain Injury With Transcranial Near-infrared Laser Phototherapy. Adv Mind Body Med. 29(4):27-33, 2015; incorporated in its entirety by reference herein). Indeed, SPECT was not used for diagnostic purposes, although an excellent case can be made for that application based on the above reviewed literature. Rather, SPECT was combined with cutting-edge quantitative analysis as a sophisticated method of detecting differences in neurological function in a patient who had undergone a specific treatment. This method demonstrates a specific treatment led to a significant improvement in cerebral function based on increased cerebral perfusion and clinical improvement in a long-standing case of chronic TBI. The data presented previously and herein lay the groundwork for our current claim to use SPECT with quantitative analysis as a tool to not only target neurological treatment, but also to detect changes in neurological function in response to said treatment.

SPECT as an Aid in Targeting a Focused Treatment to Deep Areas of the Brain

Review of the neuroimaging literature, particularly SPECT literature, on TBI has revealed that the most common areas injured in TBI are the orbitofrontal cortex (at the ventral surface of the frontal lobe) and the anterior and medial temporal lobes. It is not anatomically possible to position an NIR light emitter immediately exterior to the skull overlying these areas. An NIR light emitter must be of sufficient power to penetrate the extent of tissue intervening between the skin surface and the target tissue. For example, the orbitofrontal cortex positioned immediately above the eyes can only be reached from the forehead by angling the light emitter. Similarly, the temporal lobes are separated from the surface by epidermis, dermis, subcutaneous fat, subcutaneous blood vessels, accessory head of the temporalis muscle, connective tissue, temporalis muscle, skull, and dura mater. Each of these structures has different absorption and refraction properties, and each interface between different materials also creates a barrier to transmission of photonic energy. Blood flowing in the subcutaneous vessels is believed to create a unique barrier to transmission. In summary, effectively targeting the areas most commonly injured in TBI with sufficient photonic energy to initiate reparative processes represents a significant challenge in NILT. This appears to have been overcome with the high-power laser methodologies presented here. Penetration to the deep structures such as basal ganglia to target anxiety or to the substantia nigra to target Parkinson's disease will similarly require multi-Watt NIR lasers to be effective (Monies et al., 2015; Johnstone et al., 2016).

One concern about high-watt NIR lasers is the risk of tissue heating. We explored this issue. Temperature change was one to three degrees C. at the skin surface using continuous-wave NIR lasers in the range of 10-15 W. Using pulsed settings, the high-powered lasers showed no significant temperature change in tissue samples. The temperature change on human skin was one degree C. or less in the in vivo penetration studies while maintaining continuous movement of the laser probe head. Clinically, patients in this case series reported only slight warming of the skin, but no discomfort, using the continuous motion technique.

DETAILED DESCRIPTION

Figure 1:
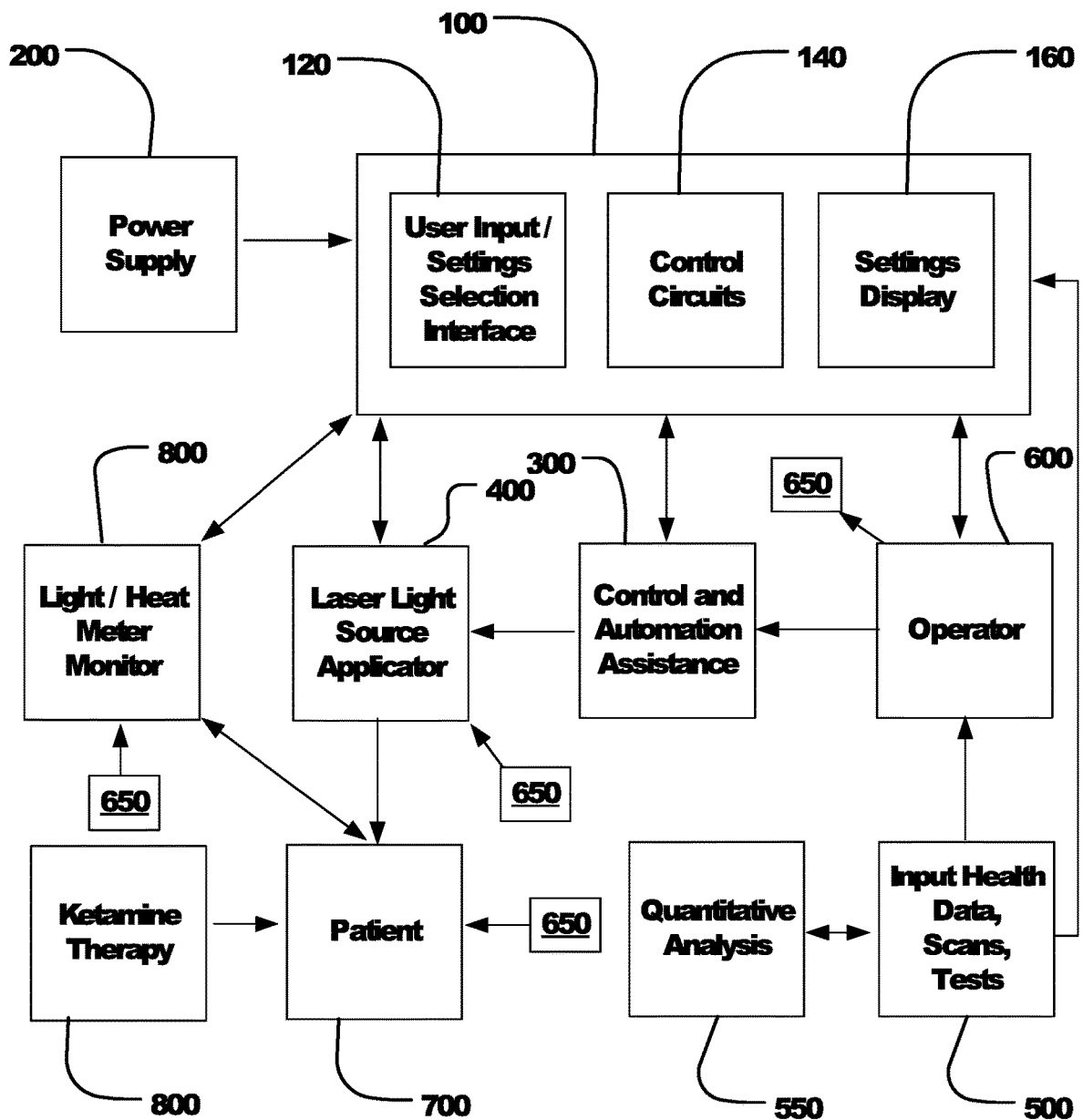
FIG. 1 illustrates an exemplary embodiment of a ketamine therapy administered to a patient in combination with an infrared light therapy system that can be utilized with one or more novel treatment methodologies.

In the following discussion, numerous specific details are set forth to provide a thorough understanding of the present disclosure. However, those skilled in the art will appreciate that embodiments may be practiced without such specific details. Furthermore, lists and/or examples are often provided and should be interpreted as exemplary only and in no way limiting embodiments to only those examples.

Exemplary embodiments are described below and in the accompanying Figures. The following detailed description provides a review of the drawing Figures in order to provide a thorough understanding of, and an enabling description for, these embodiments. One having ordinary skill in the art will understand that in some cases well-known structures, methods and functions have not been shown or described in detail to avoid unnecessarily obscuring the description of the embodiments.

Referring now to the drawings, FIG. 1 illustrates an exemplary embodiment of a ketamine therapy administered to a patient in combination with an infrared light therapy system 10 that can be utilized with one or more novel treatment methodologies. The laser control and interface unit 100 allows an operator 600 to interact with the system 10, input settings, observe the status of the unit and any ongoing procedure, etc. For example, it may be useful to set the system to output multiple wavelengths simultaneously, while being able to specify different wattages and pulsing settings for each wavelength. Subcomponents include a user input/settings selection interface 120, electronics/control circuits 140, and the settings display 160. In other embodiments one or more of the subcomponents could be relocated in other portions of the system 10 or otherwise distributed (for example, the settings display information could be displayed on a heads-up type portable display worn by the operator, on a hand-held portable electronic device such as a smart phone, projected on a nearby surface, etc.).

The user input/settings selection interface 120 allows an operator 600 to configure the system 10, specify desired system settings, input patient/procedure specific information/settings, and otherwise control the system 10 itself. The settings display 160 communicates current settings, system variables, etc. to the operator 600 so that he or she is fully informed of the system state on a real-time basis. Additional information concerning the patient, procedure, environment, etc. can also be communicated via the settings display 160.

Control circuits 140 comprise the functional electronics of the system 10 that receive user inputs/settings, configure the system accordingly, and drive the settings display 160 component. Furthermore, the control circuits 140 receive power from the power supply 200 (which can be a battery or other portable source, wall plug-in, etc.) and control the output characteristics of the laser light source applicator 400.

The laser light source applicator 400 can comprise a single applicator or a plurality of applicators. The applicators can be attached to one another or they can be moved independently from each other in some embodiments.

Control and automation assistance 300 can be software and/or hardware that assist the operator 600 in operating the laser light source applicator 400. It can automate changes in the settings, assist in movement of the applicator 400, provide for safety measures, etc. In another embodiment, no control and automation assistance 300 is present, leaving the operator to control the system 10.

The laser light source applicator 400 receives power, instructions, information and input from the laser control and interface unit 100, the control and automation assistance 300 and the operator 600 in order to generate output light with the specific characteristics desired for the particular treatment methodologies being used for a given patient 700.

The operator 600 can customize the system 10 for the needs of a particular patient based on the input health data, scans, tests, etc. 500. The SPECT scans described above can be incorporated in item 500. Additionally, Quantitative Analysis 550, as detailed above, can be applied to the SPECT scans and/or other data. The specific information (e.g, functional brain scans for brain treatment; neurodiagnostic testing for polyneuropathy, SPECT scans, Quantitative Analysis results, etc.) can help the operator and the system correctly employ the novel light therapy and ketamine therapy treatment methodologies for a particular patient 700 and his or her specific needs. A light/temperature meter monitor (e.g., laser thermometer, light meter) 800, alternatively including display and print-out capabilities 800, is used to monitor in real-time the levels of infrared light utilized as well as the patient.

The operator 600 directly interacts with the laser control and interface unit 100, the control and automation assistance 300 and other components represented by interactive 650. Interactive 650 links the operator 600 directly to the laser light source applicator 400, the light/temperature meter monitor 800, and the patient 700. FIG. 1 utilizes the interactive 650 links to represent direct interactions with these other components rather than over-complicating the figure with additional connection arrows between the operator 600 and these additional components.

A ketamine therapy 800 can be administered to the Patient 700 in combination with the infrared light therapy. As discussed in detail above, the benefits of the combined therapy are significant.

Figure 2:
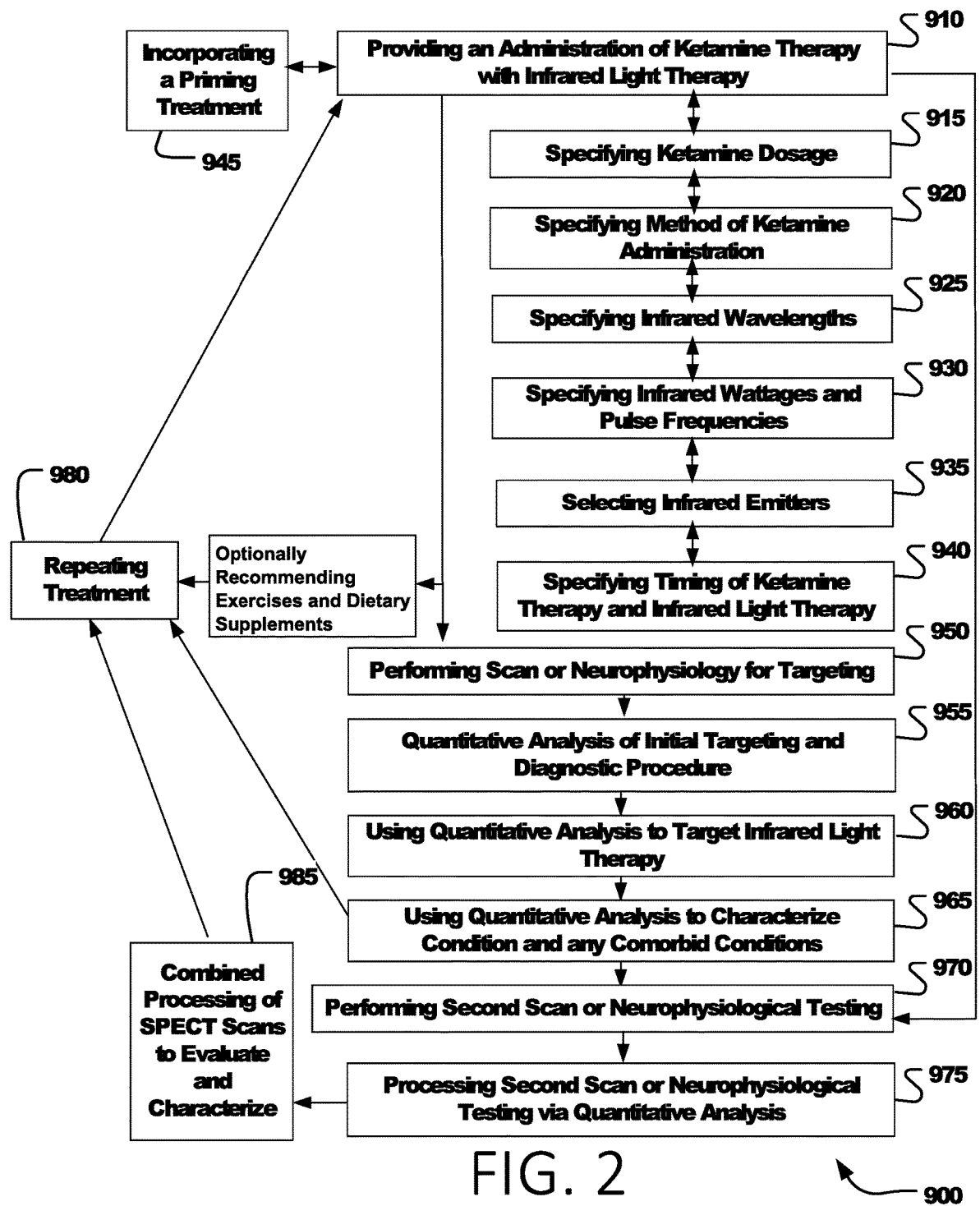
FIG. 2 is a flow chart of exemplary operations of an embodiment of novel treatment methodologies using light therapy in combination with ketamine therapy, and optionally, dietary supplements and exercise.

FIG. 2 illustrates a top plan view of exemplary operations of an embodiment of a novel treatment methodology using light therapy in combination with ketamine therapy 900. The precise mechanisms underlying photobiomodulation and its therapeutic benefits are not fully understood. However, our research continues to build the knowledge-base in this area and shed light on the mechanisms and benefits of NIR as employed in our novel treatment methodologies using light therapy.

In the embodiment illustrated in FIG. 2, an exemplary novel treatment methodology using light therapy and ketamine therapy in combination 900 is detailed in items 910-985. It should be understood by one skilled in the art that although some of the steps should occur before others, there is no strict requirement to the order of the steps and the invention may be practiced in various orders. Furthermore, although some of the steps are required, others are not, as delineated by the claims.

The step of Providing an Administration of Ketamine Therapy with Infrared Light Therapy 910 involves the appropriate and specific combination of ketamine administration and infrared light therapy. Multiple configurations are possible as described herein, and the specific combination would be determined for the particular condition being treated.

The step of Specifying Ketamine Dosage 915 involves analyzing multiple patient-specific factors to determine appropriate dosage. Ketamine dosage is determined based on patient weight, medical conditions, and the condition being treated. Ketamine therapy is administered at a dose of between 0.01 mg and 10.0 mg per kilogram of body weight of the patient. For example, in a 55 year old male without hypertension, the dose of ketamine would be 0.5 mg/kg administered intravenously over the course of 40 minutes. Other embodiments are possible and useful.

The step of Specifying Method of Ketamine Administration 920 involves determining medical conditions and the condition being treated and deciding on appropriate administration protocol. Ketamine therapy is administered to the patient by at least one of intravenously, intramuscularly, orally, and intranasally. For example, in a 55 year old male without hypertension, ketamine infusion would be controlled by an intravenous pump with monitoring of blood pressure, blood oxygenation, electrocardiogram, and end-tidal carbon dioxide. Other embodiments are possible and useful.

The step of Specifying Infrared Wavelengths 925 involves setting the laser control and interface unit 100 to the appropriate specifications for a given condition and patient. Infrared light wavelengths are determined by the condition being treated, the depth of penetration required, and other clinical factors. The selection of at least one wavelength in the range of 200 to 2000 nanometers is made. For example, in a middle-aged person, wherein deep structures of the brain are to be targeted, a wavelength of 810 nanometers would be effective. As another example, a patient being treated for neuropathy would receive a combination of 810 nanometer and 980 nanometer wavelengths delivered simultaneously along the course of the involved nerve.

Although only one particular wavelength may be desired in some instances, at other times, the operator may need to utilize two, three or more wavelengths to be delivered simultaneously, serially, etc. For example, an operator may choose to utilize multiple wavelengths (each potentially having distinct settings of pulsing and/or wattage, see below). The percentage activation of each wavelength can be variable; for example, an operator could select a 980 nm wavelength at 40% of the time, and an 810 nm at 60% of the time. Other embodiments are possible and useful.

The step of Specifying Infrared Wattages and Pulse Frequencies 930 involves setting the system to output the desired wattage(s) and frequencies for treating a given condition and patient. The duty cycle (percent of time that a pulsed light is on) may also be set in this step. Infrared light wattage is a plurality of wattages between 0.01 and 50.00 watts at the orifice of the applicator. Wattage is determined by the condition being treated, the depth of penetration required, and other clinical factors. Dosage of infrared light also is regulated by pulsing the light. Pulsing pattern and frequency is determined by the condition being treated, the depth of penetration required, and other clinical factors. The selection of pulse duration between 1 to 1000 milliseconds is made. For example, a patient being treated for an intracranial condition would receive infrared light via a laser emitter delivering 12-15 Watts at the skin surface with a pulse duration of 10 millisecond, or about 50 Hz with a 50% duty cycle. As another example, a person receiving infrared laser therapy for a neuropathy would receive 6-10 Watts at the skin surface with a pulse duration of 20 milliseconds, or about 25 Hz with a 50% duty cycle. Different pulse durations, frequencies, and duty cycles may be used should tissue heating prove to be an issue during treatment.

Because of blood flow in the tissues, temperatures at the surface and at depth generally normalize very quickly. Nevertheless, the system allows the operator to monitor temperatures and adjust the wattage, applicator motions, etc. as needed to ensure a safe temperature range (i.e., a skin temperature at 99-102 degrees F.).

The step of Selecting Infrared Emitters 935 is determined by the condition being treated, the depth of penetration required, and other clinical factors. The selection of infrared emitters is made from a plurality of stationary, moving, hand-held or computer-controlled emitters. In one embodiment, a hand held or stationary emitter is selected with a therapy window opening from one centimeter squared up to an opening of three centimeters squared. The emitters will have a glass lens of one centimeter squared up to an opening of three centimeters squared. The emitters should be limited to less than five centimeters squared for therapy purposes. Larger emitters disperse the infrared energy in an inefficient manner Other embodiments are available and are in development. Computer controlled emitters which are currently commercially available do not offer the precision of targeting necessary for most clinical applications. Stationary emitters have a limitation of higher probability of tissue heating. One excellent embodiment is a dual wave laser unit with both 810 nm and 980 nm simultaneous emission, but with individual controls for each wavelength. Selection may include one or more wavelengths. This unit also is able to control both the wattage or power to each wavelength and regulate the dosage in a pulse pattern in 1-1000 milliseconds. Specific examples of settings of wavelength and wattage are discussed in steps 925 and 930 above.

Specifying Timing of Ketamine Therapy and Infrared Light Therapy 940 is determined to ideally stimulate neurotrophic factor production and mitochondrial repair. This can involve a plurality of combinations, which can include a priming treatment (see step 945 below) with ketamine prior to administering infrared light. Other combinations include treating with ketamine between infrared light treatments and after infrared light treatments at intervals varying from one to twenty days. Another combination is to apply infrared light therapy coincident with the administration of ketamine Since each treatment stimulates neurotrophic factor production and mitochondrial repair, multiple combinations may be equally effective. The treatments can be repeated (see step 980) at intervals between one and twenty days, and for numbers of sessions greater than one, determined by the condition being treated and other clinical factors. For example, in a 55 year old male without hypertension, treating a traumatic brain injury would ideally entail physical and neurological evaluation which may or may not include a SPECT scan or neurophysiological testing. The patient would receive a series of infrared laser treatments at interval of two times per week. In addition, once per week the patient would receive an intravenous infusion of ketamine Both ketamine and infrared laser treatments activate powerful mechanisms of intrinsic healing, including but not limited to, BDNF, anti-inflammatory mediators, and numerous genes involved in healing. The sequence of alternative infrared laser treatments and ketamine infusions would alternate on an ongoing basis until the patient had received twenty infrared light treatments. A priming treatment with ketamine may be utilized as described in step 945. Re-assessment of the patient's condition may indicate further treatments as described in step 980.

The step of Incorporating a Priming Treatment 945 can be indicated in some cases. A priming treatment consists of administration of ketamine by a plurality of routes prior to initiating infrared light therapy. The interval prior to the first infrared light administration is between one and one hundred days. In an ideal example, ketamine would be administered to a patient via intravenous infusion at a dose of 0.5 mg/kg body weight over forty minutes on two separate occasions spaced at an one week interval to robustly activate the mitochondrial repair processes, which include, but are not limited to, BDNF, gene products, and anti-apoptotic mediators. These ketamine infusions are superior to oral, intramuscular, or intranasal delivery due to better absorption, better delivery across the blood-brain barrier, and more prolonged contact time with the receptors responsible for the actions of ketamine Infrared laser treatments would begin three to five days after the second infusion of ketamine in this priming embodiment.

The step of Performing Scan or Neurophysiology for Targeting 950 involves determining area(s) to be targeted. Laser-based treatment is greatly enhanced by first localizing the lesion. Laser light is highly coherent and focused. As a result, it must be aimed at the area to be treated. Performing a targeting procedure, such as a functional brain scan in the case of intracranial conditions or neurophysiological testing in the case of extra-cranial conditions, is an early step to correctly target areas requiring treatment. In certain embodiments, the targeting procedure would be conducted prior to treatment with ketamine, infrared laser, and/or both modalities. A single-photon emission computed tomography (SPECT) perfusion scan provides excellent diagnostic information on many intracranial disorders as described above. A SPECT scan also allows accurate targeting of affected areas of the brain so that the infrared laser light can be correctly applied to affected areas.

SPECT scans also provide information on comorbid conditions. In the case of spinal cord conditions and nerve-related conditions, such as neuropathy, radiculopathy, and pain, neurophysiological studies, such as electromyography and nerve conduction studies provide excellent diagnostic information. These neurophysiological studies permit mapping of the spinal or nerve involvement, characterization of the spinal or nerve involvement and identification of any comorbid conditions. Upon mapping the areas of damage or dysfunction, significantly more correct targeting of the infrared laser therapy can be employed. For example, in treating an intracranial condition, such as traumatic brain injury, in an otherwise healthy 48 year old female, the SPECT scan would be performed prior to any treatment to allow accurate targeting of the infrared laser therapy. Targeting is much less of an issue with ketamine activation of BDNF and other mitochondrial reparative agents. Processing and analyzing the scan as described in steps 955, 960, and 965 yield additional valuable targeting, diagnostic, and pathophysiological information.

The step of Quantitative Analysis of Initial Targeting and Diagnostic Procedure 955 raises the accuracy, detail, diagnostic utility, and targeting ability of the initial targeting and diagnostic procedure, whether that was a SPECT scan or neurophysiological testing. For example, to characterize an intracranial process, a SPECT is performed. A SPECT scan presented in its simplest form appears as a grey blob with little anatomical reference and poor resolution of areas of increased activity compared to areas of decreased activity. Quantitative analysis renders a SPECT scan in a color scale calibrated to the patient's peak areas of activity and increases the anatomical detail via fixation to certain reference points. The result is a clear visual picture of brain function in specific areas of the brain easily interpreted by those with experience in brain anatomy. Furthermore, analysis can be taken to additional steps of statistical comparison to a normative database. This statistical analysis yields a map of areas of difference from the normative database that are greater than two standard deviations away from the mean. Similarly, a nerve conduction study in its simplest form is an array of numbers providing little insight in the distribution, location, and extent of nerve pathology. Quantitative analysis reveals a visual map of the involvement and the extent of pathology. Quantitative analysis of scans or neurophysiological testing also provides numerical measure of the condition of the involved areas which can then be used as a baseline for measuring change step 985 in response to treatment step 910.

The step of Using Quantitative Analysis to Target Infrared Light Therapy 960 involves, in the case of intracranial conditions, using the results of the quantitative analysis of the SPECT scan to correctly target the affected areas with a focused beam of infrared light (910). In the case of extracranial conditions, the results of the quantitative analysis of the initial neurophysiological testing are used to correctly target the affected areas with a focused beam of infrared light. As alluded to in step 955, the quantitative analysis of a SPECT scan yields a detailed anatomical map of function in the brain. This provides precise targeting of the infrared light which is, by its very nature, highly coherent and focused. Similarly, quantitative analysis of neurophysiological testing provides a detailed map of the distribution of nerve involvement and areas of greatest pathology. For example, in a 63 year old woman with diabetic neuropathy of the left lower extremity, neurophysiological testing with quantitative analysis could reveal that the most severely affected section of nerve lies three centimeters from the popliteal fossa. Targeting infrared light at that location and along the distribution of the nerve inferior to that position would provide maximal benefit.

The step of Using Quantitative Analysis to Characterize Condition and Any Comorbid Conditions 965 involves applying the analysis of the SPECT scan and/or neurophysiological studies. The results of the quantitative analysis of the SPECT scan in the case of intracranial conditions are used to characterize the nature, severity, extent, and other parameters of the condition. As detailed above, SPECT can characterize several intracranial conditions. In addition, comorbid intracranial conditions can be identified by the examination of the quantitative analysis of a SPECT scan. The results of the quantitative analysis of the initial neurophysiological testing in the case of extracranial conditions are used to characterize the nature, severity, extent, and other parameters of the condition. Quantitative analysis of nerve conduction studies, electromyography, and other neurophysiological studies can also provide information on comorbid neural conditions. For example, a SPECT scan of a 62 year male with history of traumatic brain injury would reveal the location, distribution, and extent of the functional changes resulting from the brain injury, but it might also reveal overactivity of the basal ganglia, which is associated with anxiety or Post-Traumatic Stress Disorder. Alternatively, the quantitative analysis might reveal evidence of early Alzheimer's dementia characterized by decreased perfusion of the posterior cingulate gyrus, hippocampus, temporal lobes, and lateral parietal cortices.

The step of Performing Second Scan or Neurophysiological Testing 970 involves repeating the scan/testing. After one or more treatments with infrared light therapy combined with ketamine therapy, a second measure of physiology can be used to characterize change in the status or parameters of the condition being treated. The size, extent, severity, and other parameters are all measures which could change with treatment and would indicate the need for further treatment or the completion of treatment. A second or repeat SPECT scan for intracranial conditions and/or a second or repeat neurophysiological testing for extracranial conditions is performed. For example, in a 58 year male with a history of traumatic brain injury, the initial SPECT scan might have revealed profoundly decreased perfusion (function) in the right lateral frontal cortex, right insular cortex, and right anterior temporal cortex. In addition, increased perfusion (function) might have been identified in the bilateral basal ganglia (consistent with PTSD). After a course of twenty infrared light treatments using 810 nm and 980 nm at a wattage of 13 watts, combined with a priming treatment of intravenous ketamine at 0.5 mg/kg delivered over 50 minutes and four additional intravenous ketamine treatments interspersed after every third infrared light treatment, a second SPECT scan can be performed to evaluate the change in severity, distribution, location, and character of the previously identified pathology. The data would be utilized in determining whether to repeat or continue treatment and to assess the benefit of treatment to date.

The step of Processing Second Scan or Neurophysiological Testing via Quantitative Analysis 975 involves quantitative analysis processing of a second scan or neurophysiological testing. Quantitative analysis provides visual and numerical data that can be directly compared to baseline data. In the case of SPECT scans for intracranial conditions, the quantitative analysis of the two scans provides a visual map of the condition with severity demonstrated via a color scale. Direct visual comparisons of the initial and second scans can provide a visual map of the change in the size, distribution, severity, and other parameters of the condition. Moreover, quantitative analysis allows digital subtraction of the quantitative data to yield quantitative measures of the changes in the condition being treated. One of the more sophisticated and accurate of these comparison methods is described in step 985. The status, change, or development of comorbid conditions can also be characterized with a second SPECT scan.

In the case of neurophysiological testing for extracranial conditions, quantitative analysis of neurophysiological testing prior to and after one or more infrared light treatments provides a visual map of the distribution, extent, severity, and other parameters of the neural condition being treated. Quantitative analysis allows digital subtraction of the quantitative data to yield numerical measures of the changes in the neural condition after treatment. One of the more sophisticated and accurate of these comparison methods is described in step 985. The status, change, or development of comorbid conditions can also be characterized with neurophysiological testing. In the example offered in step 970, quantitative analysis of the second SPECT scan or combined processing of the two SPECT scans could reveal the significant extent of reactivation of poorly functioning tissue in the right lateral frontal cortex, right insular cortex, and right anterior temporal cortex. In addition, the overactivity in the basal ganglia may have decreased. This may or may not be completely consistent with the clinical findings and would factor into the decision to repeat or continue treatment.

The step of Repeating Treatment 980 involves repeating treatment or a modified version of the treatment. After the initial, and any subsequent, treatment with infrared light in combination with ketamine treatment, the treatment is repeated if indicated. The majority of conditions require multiple treatments with infrared light, so treatments may be repeated without intervening neurophysiological or neuroimaging assessment. After a set of treatments specified for the given condition, repeat functional neuroimaging or neurophysiological testing with quantitative analysis is performed. With or without simultaneous processing of the baseline and repeat datasets, the data from baseline is compared to the post-treatment data. If indicated, further treatment is administered. In the example offered in steps 970 and 975, an assessment would be made of the changes in the patient's subjective experience of symptoms (symptom number, severity, duration, frequency), physiological functioning assessing by clinical examination, psychological functioning assessed by clinical examination, and, if available, changes in the function of the right lateral frontal cortex, right insular cortex, and right anterior temporal cortex as revealed by SPECT scan interpretation of pre- and post-treatment scans. In consultation with the patient, the extent of recovery determined would be discussed and compared to initial goals of treatment. If further progress is desired and anticipated, then additional or repeated treatment could be employed.

The step of Combined Processing of SPECT Scans to Evaluate and Characterize 985 involves a more sophisticated form of comparison of two sets of data on brain function or neurophysiology: it is the combined or simultaneous processing of at least two datasets. By this method, variations in processing parameters are eliminated and more accurate quantitative analyses can be performed. Using simultaneous processing of SPECT scan datasets or neurophysiological testing datasets, direct numerical subtraction protocols can be applied. These quantitative subtraction analysis protocols yield delta or difference maps showing highly accurate representations of the changes in the size, distribution, severity, and other parameters of the condition being treated. By using quantitative subtraction analysis protocols, changes or emergence of comorbid conditions are accurately determined. In the example offered in steps 970 and 975, combined quantitative analysis of the two SPECT scans could reveal the quantitative extent of changes in function of the right lateral frontal cortex, right insular cortex, and right anterior temporal cortex. For example, combined processing allows quantitative subtraction imaging which would reveal a 2.3 standard deviation increase in function in the right insula, a 2.1 standard deviation increase in function of the right lateral frontal cortex, and a 1.3 standard deviation increase in function of the right anterior temporal cortex. Adjacent areas of cortex could show a similarly precise change in function by this method. In addition, the overactivity in the basal ganglia may have not only decreased, but normalized compared to a normative population database. This may or may not be completely consistent with the clinical findings and would factor into the decision to repeat or continue treatment.

Procedures for an exemplary Neuro Degenerative Patient embodiment follow.

Patient visits are generally initiated by response to a referral from other providers. The patient is interviewed to determine the history of injury, disease process, and neurodegenerative process. Neuropsychological testing may be performed. Pertinent past medical records are reviewed and medical suitability for treatment is determined. Additionally, all pertinent questions from the patient are answered, and details as as explanation of NIR therapy, SPECT Scan, length of treatment, and financial issues can be discussed.

Based on the history and medical necessity, a single photon emission computed tomography (SPECT) scan is ordered in step 950. The scan is subjected to quantitative analysis as in step 955. Results of the SPECT Scan are reviewed and localization of the injury or disease process is established as in step 960. Other pathologies may be identified as in step 965. The patient then undergoes a physical examination with emphasis of sequalae of neurological condition.

The patient may or may not receive a priming dose of ketamine by one of oral, intramuscular, intranasal, or intravenous route as in step 945. The intravenous route has the greatest benefit. In one embodiment, an intravenous line is placed in the patient's arm and ketamine is delivered intravenously under the control of an infusion pump. A dose of 0.1 to 2 mg/kg is delivered as in step 915. In one embodiment, a dose of 0.7 mg/mg is delivered over the course of 40 minutes as in step 920. The patient is monitored by a nurse anesthetist throughout the treatment and during the recovery period of 30 to 60 minutes. Blood pressure, electrocardiogram, end-tidal carbon dioxide, and pulse oxymetry also are monitored.

Either during the actual ketamine administration or thereafter, the patient is treated with near-infrared light as in step 940. In one embodiment, this would be by use of a multiwatt, hand-held laser emitter as in step 935 which is held very close to the skin and directed specifically at the areas of damage, which in some embodiments might be the frontal lobes or the temporal lobes or both in the brain.

For infrared light administration, the patient is placed on a treatment table in the supine position, with cervical pillow for comfort. The doctor and any others in attendance are given NIR protective glasses, specific to the wavelengths being used for treatment. The patient is fitted which special metal compound glasses, to block any radiation from their eyes. Then, as part of step 910, the operator configures the system. The NIR unit is then adjusted to the radiation pattern and dosage (Wattage, Wave length, Pulse Rate if any, Time, Area) as indicated for each patient as in steps 925 and 930. Infrared light is applied to the area of concern, in a circular fashion, either touching the skin or slightly off the skin. The duration of administration can vary from 1-100 minutes. In one embodiment, the administration of infrared light would be ten minutes to each area being treated (frontal lobe or two temporal lobes in one embodiment).

The infrared light administration is repeated at intervals of 1-100 days as in steps 940 and 980. In one embodiment, infrared light administration is repeated every third day. The frequency of administration can also be varied during the overall course of therapy. In one embodiment, the frequency could be reduced to every seventh day after five treatments. The total number of administrations would depend on the condition and severity and response.

The ketamine treatment also is repeated at intervals of 1-100 days as in steps 920 and 980. In one embodiment, ketamine intravenous infusion is repeated at a frequency of every seventh day. In another embodiment, ketamine oral therapy is repeated on a daily basis. The total duration of ketamine treatment may be shorter, longer, or of the same duration as the total duration of infrared light treatment.

After each infrared light administration, the patient is questioned about any reaction to therapy and any discomfort with treatment. Progress is charted based on various physiological testing instruments and diary. All charting of treatment is completed following each visit.

After a course of ketamine and infrared light treatment, the patient receives a second SPECT scan as in step 970. The second SPECT scan is quantified and compared to the first SPECT scan to establish the amount of change as in step 975. In one embodiment, the two scans are processed in parallel to allow absolute quantification of the scans and the differences between the scans as in step 985. Further treatment is provided in some embodiments based on need as in step 980.

Procedures for an exemplary Orthopedic Neuro Patient Embodiment Follow.

Patient visits are generally initiated by response to a referral from other providers. A pre-treatment interview is conducted with one of the doctors, to establish necessity of prior records, history of accident/illness, and other medical background for acceptance into the program. Additionally, all pertinent questions from the patient are answered, explanation of NIR therapy, neurophysiological testing, length of treatment, and financial issues can be discussed.

The patient is interviewed to determine the history of injury, disease process, and other nerve-related pathological process. Neurophysiological testing is performed to map the location, extent, severity, and distribution of the nerve-related pathology as in 950. The patient then undergoes a physical examination with emphasis on the nerve-related condition.

Neurophysiological testing in certain embodiments would consist of electromyography (EMG) or nerve conduction testing. Conduction velocity, amperage, onset, F-wave, H-waves, and other data provide evidence of pathology and allow the differentiation of muscle, spinal root, and peripheral nerve pathology. The data is then subjected to quantitative analysis to fully characterize the location, distribution, extent, and severity of the nerve-related pathology as in step 960. Other pathologies may be identified as in step 965.

The patient may receive a priming dose of ketamine by one of oral, intramuscular, intranasal, or intravenous route as in step 945. The intravenous route has the greatest benefit. In one embodiment, an intravenous line is placed in the patient's arm and ketamine is delivered intravenously under the control of an infusion pump. A dose of 0.1 to 2 mg/kg is delivered as in step 915. In one embodiment, a dose of 0.7 mg/mg is delivered over the course of 40 minutes as in step 920. The patient is monitored by a nurse anesthetist throughout the treatment and during the recovery period of 30 to 60 minutes. Blood pressure, electrocardiogram, and pulse oxymetry also is monitored.

Either during the actual ketamine administration or thereafter, the patient is treated with near-infrared light as in steps 910 and 940. In one embodiment, this would be by use of a multi-watt, hand-held laser emitter as in step 935 which is held very close to the skin and directed specifically at the areas of damage, which in some embodiments might be the distribution of the nerve affected by the pathology.

During the infrared light administration, the patient is placed on a treatment table in the supine position, with cervical pillow for comfort. The doctor and any others in attendance are given NIR protective glasses, specific to the wavelengths being used for treatment. The patient is fitted which special metal compound glasses, to block any radiation from their eyes. The NIR unit is then adjusted to the radiation pattern and dosage (Wattage, Wave length, Pulse Rate, Time, Area) as indicated for each patient as in steps 925, 930, and 935. Then, as part of step 910, the operator configures the system. For example, this can be accomplished by setting the wattage to 10.5 watts, setting the wavelengths to 810 nm and 980 nm, specifying continuous wave, setting duration at 10 minutes, and determining total joules to be about 6000. The operator would then activate the applicator over the nerve to be treated. Maintaining proximity and applying active circular techniques, the operator would move the applicator over the area of involvement (tracing the actual nerve/nerves, motor and sensory), from the knee to the foot (i.e., nerve tracing). The active sweeping pattern is maintained throughout, while monitoring the temperature, light, duration and patient as well. During the application of infrared light, the operator moves the treated area through a range of motion, with or without manual resistance, and other orthopedic maneuvers. The duration of administration can vary from 1-100 minutes. In one embodiment, the administration of infrared light would be twenty minutes over the distribution of the nerve being treated.

The infrared light administration is repeated at intervals of 1-100 days as in steps 940 and 980. In one embodiment, infrared light administration is repeated every third day. The frequency of administration can also be varied during the overall course of therapy. In one embodiment, the frequency could be reduced to every seventh day after five treatments. The total number of administrations would depend on the condition and severity and response.

The ketamine treatment also is repeated at intervals of 1-100 days as in steps 920 and 980. In one embodiment, ketamine intravenous infusion is repeated at a frequency of every seventh day. In another embodiment, ketamine oral therapy is repeated on a daily basis. The total duration of ketamine treatment may be shorter, longer, or of the same duration as the total duration of infrared light treatment.

After each infrared light administration, the patient is questioned about any reaction to therapy and any discomfort with treatment. Progress is charted based on various physiological testing instruments and diary. All charting of treatment is completed following each visit.

After a course of ketamine and infrared light treatment, the patient receives repeat neurophysiological testing in a manner similar to that described above as in step 970. The second set of neurophysiological testing data is quantified and compared to the first neurophysiological testing data to establish the amount of change as in step 975. In one embodiment, the two sets of data are processed in parallel to allow absolute quantification of the data and the differences between the scans as in step 985. Further treatment is provided in some embodiments based on need as in step 980.

A dietary supplement, also known as a nutritional supplement, is defined by law to be a product (other than tobacco) intended to supplement the diet that bears or contains one or more of the following dietary ingredients: a vitamin, mineral, an herb or other botanical, an amino acid, a dietary substance for use by man to supplement the diet by increasing the total dietary intake, or a concentrate, metabolite, constituent, extract, or combination of any ingredient described above. Nutritional supplements, herbs, and nootropics have been utilized for many years and are increasingly popular among the patient populations (Monies et al, 2015). There remains little clinical research on many of these agents, perhaps reflecting a lack of funding more than a lack of efficacy. Acetyl-L-Carnitine is an ester of L-carnitine and is thought to protect brain cells after injury when glucose metabolic pathways are compromised. During this period, acetyl-L-carnitine supports alternative ketogenic pathways for metabolism (Prins M L, Matsumoto J H. The collective therapeutic potential of cerebral ketone metabolism in traumatic brain injury. J Lipid Res. 2014; 55(12): 2450-7, 2014; incorporated in its entirety by reference herein). It is also believed to enhance cholinergic function. While there are several clinical studies in patients with Alzheimer's disease and preclinical data in animal models of TBI, the clinical literature on TBI remains sparse. *Ginkgo biloba* is a natural product of the tree by the same name. It has been shown to improve membrane fluidity and increase resistance to free-radical damage. It provides some subtle benefit to cognitive function in clinical studies of stroke, dementia, aging and hypoxia damage (Diamond B J, et al. *Ginkgo biloba* extract: mechanisms and clinical indications. Arch Phys Med Rehabil. 81(5):668-78, 2000; incorporated in its entirety by reference herein). It has not been systematically studied in TBI, but is used extensively in clinic, often in combination with meclofenoxate which is an avid scavenger of free-radicals (al-Zuhair H, et al. The effect of meclofenoxate with *Ginkgo biloba* extract or zinc on lipid peroxide, some free radical scavengers and the cardiovascular system of aged rats. Pharmacol Res. 38(1):65-72, 1998; incorporated in its entirety by reference herein). S-adenosylmethionine (SAMe) is a nutritional supplement which improves cell membrane fluidity and promotes the production of glutathione, an antioxidant. The benefit of SAMe has been assessed in a single clinical study of TBI (Bacci Ballerini F, et al. Treatment of postconcussion syndrome with S-adenosylmethionine. Med Clin (Barc). 80(4): 161-4, 1983; incorporated in its entirety by reference herein). Patients receiving SAMe had a 77% improvement in clinical scores of postconcussive symptoms. Citicholine provides a source of choline which can cross the blood-brain barrier. It has been used extensively in Europe and Japan as a treatment for TBI, stroke, and dementia. However, two large U.S. studies failed to demonstrate significant benefit (Bakaya M K, et al. Neuroprotective effects of citicoline on brain edema and blood-brain barrier breakdown after traumatic brain injury. *J Neurosurg.* 92(3):448-52, 2000; Zafonte R D, et al. Effect of citicoline on functional and cognitive status among patients with traumatic brain injury: Citicoline Brain Injury Treatment Trial (COBRIT). JAMA. 308(19):1993-2000, 2012; incorporated in their entirety by reference herein).

Piracetam and the related oxiracetam and phenylpiracetam have shown some promise as nootropic agents. In one double-blind, placebo-controlled study, piracetam improved several symptoms of post-concussive syndrome, including headache and vertigo (Hakkarainen H, Hakamies L. Piracetam in the treatment of post-concussional syndrome. A double-blind study. Eur Neurol. 17(1):50-5, 1978; incorporated in its entirety by reference herein). Cerebrolysin is a polypeptide that purportedly mimics the actions of neurotrophic factors (Masliah E, Diez-Tejedor E. The pharmacology of neurotrophic treatment with Cerebrolysin: brain protection and repair to counteract pathologies of acute and chronic neurological disorders. Drugs Today (Barc). 48 Suppl A:3-24, 2012; Zhang Y, et al. Improvement in functional recovery with administration of Cerebrolysin after experimental closed head injury. J Neurosurg. 118(6):1343-55, 2013; incorporated in their entirety by reference herein). Studies have shown it can reduce beta amyloid and phosphorylated tau protein accumulation. It may promote neurogenesis, synapse formation, and functional recovery (Masliah et al, 2012). In animals models of acute TBI, cerebrolysin-treated rats had more surviving neurons in the area of impact and showed greater functional recovery (Zhang et al., 2013). In a clinical trial of acute TBI, patients were recruited within 24 hours of injury and treated for three months with daily intravenous infusion of cerebrolysin. At three months, those receiving cerebrolysin performed significantly better on the Cognitive Abilities Screening Instrument (Chen C C, et al. Cerebrolysin enhances cognitive recovery of mild traumatic brain injury patients: doubleblind, placebo-controlled, randomized study. Br J Neurosurg. 27(6):803-7, 2013; incorporated in its entirety by reference herein). It remains unclear if cerebrolysin provides long-term nootropic benefit.

Omega-3 fatty acids may enhance brain repair and recovery, based on animal and clinical studies (Hasadsri L, et al. Omega-3 fatty acids as a putative treatment for traumatic brain injury. J Neurotrauma. 30(11):897-906, 2013; incorporated in its entirety by reference herein) Similarly, vitamin D may offer neuroprotective and restorative benefits (Aminmansour B, et al. Comparison of the administration of progesterone versus progesterone and vitamin D in improvement of outcomes in patients with traumatic brain injury: A randomized clinical trial with placebo group. Adv Biomed Res. 1:58, 2012; incorporated in its entirety by reference herein) in the acute TBI setting. In chronic TBI, vitamin D and omega-3 fatty acids may work synergistically, as they both may reduce neuroinflammation, apoptosis, and oxidative stress (Scrimgeour A G, Condlin M L. Nutritional treatment for traumatic brain injury. J Neurotrauma. 2014; 31(11):989-99, 2014; incorporated in its entirety by reference herein). A six month trial of ginkgo, vinpocetine, acetyl-L-carnitine, huperzine, alpha-lipoic acid, n-acetylcysteine, multi-vitamins, and over 5 grams of omega-3 fatty acids daily yielded improved performance on cognitive testing and increased perfusion (function) on Single-Photon Emission Computed Tomography (SPECT) scan (Amen D G, et al. Reversing brain damage in former NFL players: implications for traumatic brain injury and substance abuse rehabilitation. J Psychoactive Drugs. 43(1):1-5; 2011; incorporated in its entirety by reference herein). Long term use of Dietary Flavanols may improve cognition in mild TBI (Monies et al., 2015; Theadom A, Mahon S, Barker-Collo S, McPherson K, Rush E, Vandal A C, et al. Enzogenol for cognitive functioning in traumatic brain injury: a pilot placebo-controlled RCT. Eur J Neurol. 20(8):1135-44, 2013; incorporated in its entirety by reference herein).

Growing evidence supports the contention that TBI, even mild TBI or concussion, can lead to accumulation of tau protein in the cerebral cortex (Tagge C A, et al., Concussion, microvascular injury, and early tauopathy in young athletes after impact head injury and an impact concussion mouse model. Brain. 141(2):422-458, 2018; Kulbe J R, Hall E D. Chronic traumatic encephalopathy-integration of canonical traumatic brain injury secondary injury mechanisms with tau pathology. Prog Neurobiol. 158:15-44, 2017; incorporated in their entirety by reference herein). Tau protein deposition is a pathological hallmark of Chronic Traumatic Encephalopathy (CTE), which is believed to lead to mood dysregulation, cognitive impairment, dementia, and suicide as it progressively worsens over time (Stern R A, et al. Clinical presentation of chronic traumatic encephalopathy. Neurology. 81(13):1122-1129, 2013; McKee A C, et al. The spectrum of disease in chronic traumatic encephalopathy. Brain. 136(1):43-64, 2013; incorporated in their entirety by reference herein). Tau accumulation results from hyperphosphorylation of the tau protein into an insoluable deposit (McKee et al., 2013). Two key proline-directed kinases (glycogen synthase kinase-3 {GSK-3} and cyclin-dependent kinase-5 {CDK-5}) promote the hyperphosphorylation of tau proteins (Noble W, et al, Inhibition of glycogen synthase kinase-3 by lithium correlates with reduced tauopathy and degeneration in vivo. PNAS 102:6990-6995, 2005, incorporated in its entirety by reference herein) Inhibitors of GSK-3 or CDK-5 have the potential of decreasing or preventing tau protein accumulation by preventing hyperphosphorylation. Lithium, in ionic form or organically bound form, is a GSK-3 inhibitor. Dietary supplementation of lithium chloride, at doses resulting in sub-therapeutic blood levels, has been shown to inhibit tau protein aggregation and related degeneration. Transgenic mice which overexpress tau protein were treated with lithium chloride with resulting blood levels at or below 0.2 milli-Equivalents per liter and showed significantly decreased levels of tau protein accumulation upon pathological examination (Noble et al., 2005; Engel T et al., Chronic lithium administration to FTDP-17 tau and GSK-3b overexpressing mice prevents tau hyperphosphorylation and neurofibrillary tangle formation, but pre-formed neurofibrillary tangles do not revert. J Neurochem. 99:1445-1455, 2006; incorporated in its entirety by reference herein). These data support the concept that dietary supplementation with lithium with in the form of ionic lithium chloride or organic lithium oratate, at doses below those used in the psychiatric treatment of depression or bipolar disorder, may prevent the progressive damage of tau accumulation known to occur in TBI, Alzheimer's disease, Parkinson's disease (Winer J R et al. Associations Between Tau, β-Amyloid, and Cognition in Parkinson Disease. JAMA Neurol. 75(2):227-235, 2018; incorporated in its entirety by reference herein), multiple sclerosis (Mellergard J et al. Cerebrospinal fluid levels of neurofilament and tau correlate with brain atrophy in natalizumab-treated multiple sclerosis. Eur J Neurol. 24(1) 112-121, 2017; incorporated in its entirety by reference herein) and possibly other neurological disorders. "Low-dose lithium" refers to administration of less than 100 mg of lithium metal to a patient, whether in ionic form or in a salt.

Natural anthocyanins have been shown to protect the brain from oxidative stress and mitochondrial dysfunction (Lu J et al, Purple sweet potato color alleviates D-galactose-induced brain aging in old mice by promoting survival of neurons via PI3K pathway and inhibiting cytochrome C-mediated apoptosis. Brain Pathol. 20(3): 598-612, 2010, incorporated in its entirety by reference herein). Purple sweet potato color provides a naturally occurring anthocyanin and has been shown to enhance recovery of brain function and memory after injury (Wu D M et al. Purple sweet potato color repairs d-galactose-induced spatial learning and memory impairment by regulating the expression of synaptic proteins. Neurobiol Learn Mem. 90(1):19-27, 2008; incorporated in its entirety by reference herein). Underlying mechanisms include activation of nuclear factor kappa B, which is a redox sensitive transcription factor (Shan Q et al. Purple sweet potato color ameliorates cognition deficits and attenuates oxidative damage and inflammation in aging mouse brain induced by d-galactose. J. Biomed Biotechnol. 2009:564737, 2009; incorporated in its entirety by reference herein). This pro-survival transcription factor modulates the expression of numerous genes, including ones involved in inflammation, early response, and cell survival. As a consequence anthocyanins, such as purple sweet potato color, can augment or supplement the molecular actions of near-infrared phototherapy in both the mitochondria and the cell nucleus.

In summary, nutritional supplementation with a number of different supplements have shown benefit in diseases related to mitochondrial dysfunction and/or neurotrophic factor deficiency. A single supplement by itself may have a small beneficial effect, but when combined with the powerful effects of infrared light on mitochondrial function and neurotrophin production, the effect may be magnified. The combination of nutritional supplementation and infrared light treatment may be synergistic. Combining this potential synergism with the demonstrated synergism of near infrared light treatment and ketamine administration may provide further synergistic benefit.

Exercise training in combination with NILT has a synergistic effect in the treatment of neurodegenerative and neuro-traumatic injuries. In general, exercise is good for everyone. Its many benefits include increasing the ability to move, improving balance, increasing the flexibility of joints, improving mood, and decreasing levels of depression and anxiety. Exercise has also been shown to decrease or slow the onset of diabetes and heart disease. Most importantly, the overall effect of exercise is to increase energy production in the body.

In mitochondrial dysfunction disorders, exercise can give a patient more energy on a biochemical level. Exercise increases the number of healthy mitochondria in the cells by turning on the genes that make mitochondria. One might ask, however, does this also increase the unhealthy or mutated mitochondria in the cells? If the mutation is nuclear, then no, the number of unhealthy mitochondria would not be increased. If it is a mitochondrial mutation, then exercise may increase the unhealthy mitochondria, but because more ATP is also being produced, it is still better to exercise and increase energy production.

Research has demonstrated that exercise increases neurotrophins in the brain and elsewhere. For example, exercise has been shown to promote neurotrophin production and reduce inflammation (Cotman C W et al., Exercise builds brain health: key roles of growth factor cascades and inflammation. Trends in Neurosciences. 2007; 30:464-472; Mackay C P, et al., The Effect of Aerobic Exercise on Brain-Derived Neurotrophic Factor in People with Neurological Disorders: A Systematic Review and Meta-Analysis. Neural Plast. 2017; 2017:4716197. Incorporated in their entirety by reference herein). BDNF production is specifically enhanced with exercise and this appears to be mediated by increased levels of beta-hydroxybutyrate (Sleiman S F et al., Exercise promotes the expression of brain derived neurotrophic factor (BDNF) through the action of the ketone body β-hydroxybutyrate. Elife. 2016 Jun. 2; 5. pii: e15092. Incorporated in its entirety by reference herein).

Research indicates that exercise makes the body use oxygen more efficiently and increases exercise tolerance and metabolism. There is some evidence that resistance exercise (pulling or pushing against some force) actually diluted the unhealthy or mutant load of mitochondria in muscle cells.

An exercise rehabilitation strategy for people with Parkinson's disease, MS, AD, PTSD, TBI and other diseases resulting from mitochondrial dysfunction or neurotrophin deficiency may provide additional improvement in function. Generalized rehabilitation training of amplitude in the limb motor system may reduce bradykinesia and hypokinesia in the upper and lower limbs in subjects with Parkinson disease across disease severity. (Farley B G. Training BIG to move faster: the application of the speed-amplitude relation as a rehabilitation strategy for people with Parkinson's disease. Exp Brain Res (2005) 167: 462-467. Incorporated in its entirety by reference herein.) Training is unique in that it applies well-established treatment concepts from a proven treatment for the speech motor system in PD to the limb motor system and the hypothesis that the training of exaggerated large amplitude (Full Range of Motion) movements involving the full body would impact its effects on both the upper and lower extremities. Exercise principles such as large movements of these extremities and speed of movement has a secondary effect on amplitude and speed of movement during routine activities, such as walking and reaching. By improving balance and coordination, PD patients can improve their quality of life.

Exercise also improved gait speed and cognitive function in MCI Mild cognitive impairment. (Lipardo D S et al., Effect of Exercise and Cognitive Training on Falls and Fall-Related Factors in Older Adults with Mild Cognitive Impairment: A Systematic Review. Arch Phys Med Rehabil 2017 October 98(10):2079-2096. Incorporated in its entirety by reference herein).

Regular physical exercise has been proved to have therapeutic benefit, such as treating psychiatric illnesses, supporting brain injury recovery, and resisting neurodegenerative diseases. Effects attributed increased capacities of metabolism reserve and antioxidation. The regulation of secretion of neurotrophic factors, vasculotropic factors, inflammatory mediators, neurotransmitters are also induced by exercise resulting in a beneficial influence on brain function (Lin T W, et al. Exercise benefits brain function: the monoamine connection. Brain Sci. 2013 Jan. 11; 3(1):39-53. Incorporated in its entirety by reference herein).

Exercise is in particular known to reduce disability and improve quality of life in persons with Parkinson disease ("PD"). While many forms of exercise are beneficial, PD affects control over the body and poses special challenges for patients. Low outcome expectation of exercise, lack of time to exercise, and fear of falling appear to be important perceived barriers to engaging in exercise among ambulatory, community-dwelling persons with PD. Thus a program of exercise that addresses these concerns is highly beneficial.

The inventors have developed a specific exercise program to address these concerns, known by the acronym: PERKS: Parkinson Exercises and Rehabilitation Klass. The clinical use of this program has shown significant functional improvement in patients with PD while keeping the strain and risk of injury low. The program goals include: 1. Improve Posture, 2. To stabilize core musculature, 3. To enhance spinal and neurological health, 4. To prevent spinal issues.

The PERKS program consists of a series of thirty-four simple, relatively low stress movements, all of which are designed to improve balance and coordination. For the purposes of this application, the term "PERKS exercise" should be understood to refer to any one of the individual exercises described below. The term "PERKS program" should be understood to refer to the entire group of exercises. In addition, each exercise is given a name at the beginning of the paragraph describing it, and it will be understood that for the purposes of this application, any reference to a name found in one of the following paragraphs refers to the series of movements that immediately follow it.

Tilting Posture Warm-up. 1) Standing with arms held at the side and feet spread to shoulder width, the patient pulls belly button in towards their spine by tightening the abdominal muscles. 2) Facing forward, place one hand in the air while keeping the other arm at body side. Breathe in while slowly stretching the upraised arm over the head towards the opposite side of the body, while slowly bedding the trunk towards the opposite side and sliding the hand held at the side of the body down the thigh for stability. 3) Relax at the end of the stretch, breathing in and out five times. 4) Switch to the opposite side of the body and repeat. 5) Perform the movement twice for each side of the body.

Twisting Posture Warm-up. 1) Standing with arms held at the side and feet spread to shoulder width, the patient pulls belly button in towards their spine by tightening the abdominal muscles. 2) Raise the arms to shoulder height on both sides. 3) Rotate arms at the elbow in the vertical direction ('hands up" position). 4) Bring left elbow across torso towards right knee while raising the right knee as far as is comfortable. 5) Return to the starting "hands up" position. 6) Repeat the movement with the right elbow and left knee. 7) Repeat maneuver for 15 seconds.

Eagle Warm-up. 1) Standing with arms held at the side and feet spread to shoulder width, the patient pulls belly button in towards their spine by tightening the abdominal muscles. 2) Slowly raise arms and pull shoulder blades together. 3) While taking a breath in, raise arms until the hands touch over the head. 4) Slowly lower the arms to the side of the body while breathing out. 5) Repeat two times.

Hummingbird Warm-up. 1) Standing with arms held at the side and feet spread to shoulder width, the patient pulls belly button in towards their spine by tightening the abdominal muscles. 2) Raise the arms to shoulder height on both sides. 3) Rotate arms at the elbow in the vertical direction ('hands up" position). 4) Make small backwards circles with arms and hands and sway side to side. 5) Continue this motion for 15 seconds.

Banging the Gong: 1) Standing with arms held at the side and feet spread wider than shoulder width, the patient pulls belly button in towards their spine by tightening the abdominal muscles. 2) Bend the elbows and raise the forearms to slightly above waist level on both sides. 3) Twist the torso about the spine gently side to side while breathing calmly and deeply. 4) Continue this motion for 15 seconds.

Cervical rotation. 1) Standing with arms held at the side and feet spread to shoulder width, the patient pulls belly button in towards their spine by tightening the abdominal muscles. 2) Gently turn head without moving shoulders to the right and then to the left without causing discomfort. 3) Gently tilt head upwards and then downwards while looking first up and then down.

Eye Movement. 1) Look up to the ceiling without moving the head. 2) Hold for 10 seconds. 3) Look down to the floor without moving the head. 4) Hold for 10 seconds. 5) Look to the right without moving the head and hold for 10 seconds. 6) Look to the left without moving the head and hold for 10 seconds.

Seated Body Rotation. 1) In a seated position on a chair without arms, fold arms so hands are on opposite shoulder. 2) Slowly rotate body to the right and hold for 10 seconds. 3) Slowly rotate body to the left and hold for 10 seconds.

Shoulder Shrugs. 1) Standing with arms held at the side and feet spread to shoulder width, the patient pulls belly button in towards their spine by tightening the abdominal muscles. 2) Shrug shoulder up and forward. 3) Hold position for 10 seconds. 4) Pull shoulders back and up. 5) Hold for 10 seconds. 6) Repeat five more times.

Combined Wrist Extension and Flexion. 1) From a comfortable sitting or standing position, grip hands together and bend the right wrist back and the left wrist forward. 2) Relax and then bend left wrist back and right wrist forward.

Separate Wrist Extension and Flexion. 1) From a comfortable sitting or standing position, bend one wrist backwards gently and hold for 10 seconds. 2) Repeat maneuver with other wrist. 3) Raise one arm and slowly and gently bend one wrist in flexion and hold for 10 seconds. 4) Repeat maneuver with other wrist.

Leg lift and Stomp. 1) Sitting straight in a chair with no arms, light right leg in a bent position as is comfortable. 2) Stomp the leg down to floor while yelling "Stomp". 3) Repeat with left leg. 4) Repeat maneuver five more times.

Arising from Sitting—45 Degrees. 1) From a sitting position in a chair with no arms, first bend forward about 45 degrees, then lift body to a standing position. 2) Bend forward at waist and sit back down. 3) Repeat maneuver twice.

Sitting Extension. 1) From a sitting position with feet flat on floor, hold arms over head and lean backwards gently. 2) Repeat maneuver twice.

Cross Over the Chair. 1) Standing by a chair with arms held at the side and feet spread to shoulder width, the patient pulls belly button in towards their spine by tightening the abdominal muscles. 2) Step with right leg to the right side of chair. 3) Bring left leg together with right leg so then standing beside chair. 4) Step back with left foot. 5) Bring left foot around in front of chair so feet are at shoulder width and even. 6) Repeat with other side.

Standing Rock-in. 1) Standing erect, rock up on toes eight times. 2) Then rock gently onto heels eight times.

Standing Twist. 1) Standing with arms held at the side and feet spread to shoulder width, the patient pulls belly button in towards their spine by tightening the abdominal muscles. 2) Raise both arms to shoulder height. 3) Gently twist at the waist to the right and then to the left. 4) Repeat four more times.

Upper Body Twist with Foot Turn. 1) Standing with arms held at the side and feet spread to shoulder width, the patient pulls belly button in towards their spine by tightening the abdominal muscles. 2) Raise both arms to shoulder height. 3) Gently twist the upper body to the right and allow left foot to pivot. 4) Gently twist the upper body to the left and allow the right foot to pivot. 5) Repeat maneuver four more times.

Cross Body and Reach. 1) Standing with arms held at the side and feet spread to shoulder width, the patient pulls belly button in towards their spine by tightening the abdominal muscles. 2) Extend the right hand over the left knee. 3) Raise right arm up and forward from the knee and rotate about the shoulder until arm is above head and fully extended to the right. 4) Repeat maneuver with the left arm over the right knee. 5) Repeat exercise four more times.

Shoulder Dowel Exercises. 1) Standing with feet spread to shoulder width, the patient pulls belly button in towards their spine by tightening the abdominal muscles. 2) Grasp a dowel in both hands with an overhand grip. 3) Raise both arms to shoulder height. 4) Extend to full extension of right and then sweep the dowel in form of the body to shift to full extension on the left. 5) Repeat maneuver four more times.

Dowel Shoulder Stretch. 1) Standing with feet spread to shoulder width, the patient pulls belly button in towards their spine by tightening the abdominal muscles. 2) Grasp a dowel in both hands with an overhand grip. 3) Raise both arms over the head with full extension. 4) Twist gently to right and then to left. 5) Bring dowel into vertical position in front of body. 6) Repeat maneuver four more times.

Dowel Overhead Sweep. 1) Standing with feet spread to shoulder width, the patient pulls belly button in towards their spine by tightening the abdominal muscles. 2) Grasp a dowel in both hands with an overhand grip. 3) Raise both arms to hold dowel over the head. 4) Sweep dowel down to left side of body at waist level. 5) Raise dowel over the head. 6) Sweep dowel down to right side of body at waist level. 7) Repeat maneuver four more times.

Overhead Dowel Twist. 1) Standing with feet spread to shoulder width, the patient pulls belly button in towards their spine by tightening the abdominal muscles. 2) Grasp a dowel in both hands with an overhand grip. 3) Raise both arms to hold dowel over the head with full arm extension. 4) Twist gently at the waist to the left and then to the right. 5) Repeat maneuver four more times.

Shoulder Abduction. 1) Standing with feet spread to shoulder width, the patient pulls belly button in towards their spine by tightening the abdominal muscles. 2) Start with right hand on left wrist at hip level. 3) Raise and extend right hand over right shoulder with full extension. 4) Return to neutral position. 5) Place left hand on right wrist and hip level. 6) Raise and extend left hand over left should with full extension. 7) Repeat maneuver four more times.

Crossing the Midline. 1) Standing with feet spread to shoulder width, the patient pulls belly button in towards their spine by tightening the abdominal muscles. 2) Place right hand on left knee. 3) Return to neutral position. 4) Place left hand on right knee. 5) Return to neutral position. 6) Place right hand on left hip. 7) Return to neutral position. 8) Place left hand on right hip. 9) Return to neutral position. 10) Raise right hand over the head. 11) Return to neutral position. 12) Raise left hand over the head. 13) Return to neutral position.

Back Foot Rock; Forward Foot Rock. 1) Standing with feet together, the patient pulls belly button in towards their spine by tightening the abdominal muscles. 2) Place the right foot approximately one foot length behind the left foot. 3) Rock backwards on the right foot gently. 4) Reverse foot position and repeat maneuver. 5) Return to neutral position. 6) Place the right foot approximately one foot length in front of the left foot. 7) Rock forwards on the right foot gently. 8) Reverse foot position and repeat maneuver.

Deep Bow. 1) Standing with feet together, the patient pulls belly button in towards their spine by tightening the abdominal muscles. 2) Reach high with both hands over the head. 3) Step forward with one foot. 4) Brings arms in front of body but keeping them at should height or above. 5) Lean forward while moving arms behind body with arms and legs straight. 6) Repeat two more times.

Lunges into It. 1) Standing with feet at shoulder width, the patient pulls belly button in towards their spine by tightening the abdominal muscles. 2) Lift right leg high and lunge forward. 3) Stomp right foot down and yell "Stomp". 4) Return right foot to neutral position and shout "Back". 5) Return to starting position. 6) Repeat with left foot. 7) make five repetitions for each side.

Side Stomp and Lunge. 1) Standing with feet slightly apart, the patient pulls belly button in towards their spine by tightening the abdominal muscles. 2) Take a large side step to the right and yell "Stomp". 3) Return to starting position. 4) Take a large side step to the left and yell "Stomp". 5) Repeat maneuver 10-20 times. 6) Lunge with right foot to the side and yell "Stomp". 8) Repeat with left foot. 9) Repeat maneuver four more times.

Forward and Back Lunges. 1) Standing with feet slightly apart, the patient pulls belly button in towards their spine by tightening the abdominal muscles. 2) Hold arms and hands back and step forward with right foot and yell "Stomp". 3)

Step back with right foot and yell "Stomp". 4) Return to starting position. 5) Repeat with left foot. 6) Repeat maneuver four more times.

Bowing Right and Left. 1) Standing with feet slightly apart, the patient pulls belly button in towards their spine by tightening the abdominal muscles. 2) Step forward with right foot and bend at the waist while keeping back straight. 3) Return to starting position. 4) Repeat with left foot. 5) Repeat maneuver four more times.

Wall Push Up. 1) Standing with feet at shoulder width, the patient pulls belly button in towards their spine by tightening the abdominal muscles. 2) Place hand on wall just above shoulder level. 3) Position feet 12 inches from wall. 4) Lean into wall so nose can touch wall while keeping feet still. 5) Return to starting position. 6) Repeat nine more times.

Wall Side Bridge. 1) Standing with feet at shoulder width, the patient pulls belly button in towards their spine by tightening the abdominal muscles. 2) Place hand on wall just above shoulder level. 3) Position feet 12 inches from wall. 4) Move the right hand off the wall while rotating the body to the right. 5) Return to neutral position. 6) Move the left hand off the wall while rotating the body to the left. 7) Return to neutral position. 8) Repeat maneuver five more times.

Motor Tuning. 1) In a seated position in a chair without arms. Place hands on knees. 2): Lift right hand and right foot together. 3) Lower right hand and foot. 4) Repeat four more times. 5) Lift left hand and left foot together. 6) Lower left hand and foot. 7) Repeat four more times. 8) Raise both hands and both feet simultaneously. 9) Lower both hands and both feet. 10) Repeat four more times. 11) Raise the right hand and the left foot together. 12) Lower hand and foot. 13) Repeat four more times. 14) Raise left hand and right foot together. 15) Lower hand and foot. 16) Repeat four more times.

The PERKS program, as described above, is possible for many PD patients and aids in the development of both balance and coordination, which are known to be serious problems for patients with PD.

Alterations in structure and function occur in the brain impacted by mitochondrial dysfunction or neurotrophin deficiencies, such as Dementias, MS and Parkinson's Disease. Executive function is preferentially affected as the brain suffers greater disease progression—and executive function is more prone to traumatic neurological insult. Older adult brains have some capacity that can be modified by aerobic exercise. Functional re-organization of sensory and motor pathways following injury is a widely documented phenomenon. Effects of Exercise include: 1) increased brain volume and function, 2) less cognitive function decline, 3) less motor function decline, 4) less decline in complex tasks and daily function. The present invention relates to injury, disease, and dysfunction of the brain, spinal cord and/or nerves. In any situation in which this occurs, treatment and repair of the injury, disease, or dysfunction of the brain, spinal cord, and/or nerves can be approached with infrared light NILT as a treatment modality.

Additional steps that can be a part of embodiments of the methods include the following items.

Conducting a Preliminary Appointment with the patient wherein the patient is selected based on indications and absence of contraindications. The patient is informed of what to expect from the treatment, information about the light and ketamine therapy, possible contraindications, alternate treatment options, etc. The patient can be asked to complete a questionnaire regarding medications, activities, allergies to ketamine and/or infrared light, etc. Additionally, a patient may undergo diagnostic testing or imaging (SPECT or MRI) to aid in the localization of the area requiring treatment. A discussion of the area(s) to be specifically treated and why, based upon a SPECT scan or other diagnostic information, is conducted. The patient is also informed of the potential number of appointments to expect for treatments related to their condition; and any manufacturer's brochures and other information is distributed.

Positioning and Preparation can involve preparing the patient for the treatment, including ensuring that no lotions or oils are present and removing or shortening hair in the region to be treated (cut to less than ½ inch or shaved), The patient is then positioned comfortably on a treatment table and the area to be treated is made fully accessible. Proper head support is important, especially when the head is to be treated.

Enhancing Safety involves ensuring that patient, operator, and anyone else in the room dons appropriate safety gear. Protective eyewear should be worn, which will include metal safety goggles, especially for the patient. The operator wears protective eyewear that is customized to be specific to the wavelength(s) of the system.

Specifying Pulsing involves setting the system to output the NIR light in a non-continuous or pulsed mode. When the operator wishes to decrease the temperature of the treated area, he or she can vary the pulse rate; for example, choosing a longer rest period will cause the temperature to decrease. Alternatively, decreasing the therapeutic period can also cause the temperature to decrease. The operator can utilize the system to control how long either period of the pulse lasts. Pulsing of infrared light also increases the depth of penetration and the amount of energy delivered to any given point at the peak of a pulse. Yet, pulsing allows for troughs of energy output such that the overall energy delivered to the tissue can be equivalent or even lower than that delivered by a continuous emission.

Duration involves determining the length of time of a given treatment. The time varies depending on the area to be treated, patient parameters (e.g., the size of the head, which is mostly dependent on age and sex of individual; tissue bulk overlying a joint to be treated, etc.), and therapeutic response. The standard treatment time is often less than 30 minutes, but can be longer as needed.

Specifying Total Joules involves determining the total Joules to be delivered during the treatment. This can be calculated based on wattage, pulsing, treatment duration, and area to be treated; adjustments can be made thereto in order to adjust the total Joules desired.

Specifying Treatment parameters and area involves measuring the area to be treated and recording it in the chart.

Activating Applicator involves the operator actually activating the laser light and applying the applicator to the patient's skin (or in close proximity thereto, about zero to ten millimeters). In one embodiment, the laser light source applicator 400 comprises a single applicator; in another embodiment, it comprises a plurality of applicators. The applicators can be attached to one another or they can be moved independently from each other in some embodiments.

Maintaining Proximity and Applying Active Circular Techniques involves the operator maintaining the applicator in contact with the skin or in close proximity thereto; yet, at the same time, maintaining the applicator in continuous motion. A finger or applicator distance device can be used to assist the operator in maintaining the appropriate distance between the applicator and the skin. As the distance between the applicator and the patient's skin increases, the increasing amount of air that the laser must pass through causes a decrement in the power of the laser light. This loss of photonic energy significantly decreases the amount of tissue penetration and reduces the efficacy of the treatment. During application of the light, the operator can apply an active circular motion technique to keep the applicator moving in overlapping circles having approximately 50% overlap and moving linearly from one circle to the next. The distance covered in the overlapping circular motion depends on the size of the applicator; in one embodiment circles with diameters of approximately 1-3 centimeters can be used. In other embodiments, non-circular application techniques can be utilized, such as a "stroking" motion.

Applying in Active Sweeping Pattern involves the operator applying the applicator to the patient while moving linearly across (or down) the treatment area, followed by offsetting with a 50% overlap and sweeping back the other direction. This active sweeping pattern comprises a continuous sweeping motion that is maintained in order to minimize heat build-up and/or patient discomfort. The active sweeping pattern continues until the entire treatment area has been traversed. In some embodiments, multiple traversals of the treatment area are required. In yet other embodiments, other patterns/types of applications are contemplated.

Monitoring Temperature, Light, Duration, Patient: involves the operator and the system monitoring multiple items including the temperature of the patient's skin, the light power output, the duration of the treatment, and the patient. This can be an ongoing step throughout the treatment. A laser thermometer and other monitoring devices can be integrated into the applicator or be separate components.

Review and Scheduling involves reviewing the treatment with the patient, interviewing the patient about his or her condition and experiences during the treatment and scheduling future treatments (as most conditions require multiple treatment sessions).

In one embodiment, the inventive method can be employed to treat an exemplary case of polyneuropathy. In this example, a neurologist or other medical professional can conduct an EMG study (or other diagnostic procedure) to determine which nerve is involved, locate the distal portion of the nerve and the path through the body. Then, after the appropriate ketamine administration, as part of 910, the operator configures the system. For example, this can be accomplished by setting the wattage to 10.5 watts, setting the wavelengths to 810 nm and 980 nm, specifying continuous wave, setting duration at 10 minutes, and determining total joules to be about 6000. The operator would then activate the applicator over the nerve to be treated. Maintaining proximity and applying active circular techniques, the operator would move the applicator over the area of involvement, tracing the actual nerve or nerves involved. This might entail, for instance, moving from the hip down the leg to the foot, or from the hand up the arm to the shoulder. The active sweeping pattern is maintained throughout, while monitoring the temperature, light, duration and patient as well. The treatment is then reviewed with the patient and follow-up treatments are scheduled (usually approximately 9-10 treatments for this condition). Data from past treatments as above have shown a 20-30% increase in the conduction velocity of the nerves involved.

In summary, during NIR phototherapy, absorption of red or NIR photons by COX in the mitochondrial respiratory chain causes secondary molecular and cellular events, including activation of second messenger pathways, changes in NO levels, and growth factor production. NILT leads to the reduction of excitotoxicity, the production of neurotrophic factors, the modulation of ROS, the transcription of new gene products with protective or pro-proliferative properties, and the release of numerous growth factors for neurons and other cells. NIR appears to initiate a cascade of subcellular events which can yield immediate, delayed, and persistent beneficial changes in the injured neuron or other cell. [NOTE: include ketamine and SPECT]

Extensive research has shown that fluence within the range of 0.9-15.0 $J/cm^2$ is most effective in activating the biological processes involved in reversing or mitigating the pathophysiological effects of TBI. The attenuation of NIR energy as it passes through tissue has been examined in computer simulations, animal tissue, and human tissue. NIR penetration to the human brain is subject to attenuation by multiple tissues (skin, skull, dura, blood, cerebrospinal fluid) and multiple interfaces which scatter, absorb, and reflect the NIR light to varying degrees. We have shown through the use of higher wattage NIR lasers that we can deliver fluence at therapeutic levels to the depths of the brain without tissue heating or damage. The protocols have been applied in our clinic with excellent clinical results and no side effects.

As an example, review of the neuroimaging literature on TBI has revealed that the most common areas injured in TBI are the orbitofrontal cortex (at the ventral surface of the frontal lobe) and the anterior and medial temporal lobes. An NIR light emitter must be of sufficient power to penetrate the extent of tissue intervening between the skin surface and the target tissue. For example, the orbitofrontal cortex positioned immediately above the eyes can only be reached from the forehead by angling the light emitter. Similarly, the temporal lobes are separated from the surface by epidermis, dermis, subcutaneous fat, subcutaneous blood vessels, accessory head of the temporalis muscle, connective tissue, temporalis muscle, skull, and dura mater. Each of these structures has different absorption and refraction properties, and each interface between different materials also creates a barrier to transmission of photonic energy. Blood flowing in the subcutaneous vessels is believed to create a unique barrier to transmission. In summary, effectively targeting the areas most commonly injured in TBI with sufficient photonic energy to initiate reparative processes represents a significant challenge in NILT. This appears to have been overcome with the high-power laser methodologies presented here. Penetration to the deep structures such as basal ganglia to target anxiety or to the substantia nigra to target Parkinson's disease will similarly require multi-Watt NIR lasers to be effective (Monies et al., 2015; Johnstone et al., 2016).

One concern about high-watt NIR lasers is the risk of tissue heating. We explored this issue. Temperature change was one to three degrees C. at the skin surface using continuous-wave NIR lasers in the range of 10-15 W. Using pulsed settings varying between 10 and 1000 Hz at a 50% duty cycle, the high-powered lasers showed no significant temperature change in tissue samples. Where heating is a problem, reduced duty cycles as low as 10% can also be used, although these require additional treatment time to achieve the necessary fluence. The temperature change on human skin was one degree C. or less in the in vivo penetration studies while maintaining continuous movement of the laser probe head. Clinically, patients in this case series reported only slight warming of the skin, but no discomfort, using the continuous motion technique.

Ketamine has been shown to increase BDNF in numerous laboratory studies and the clinical picture supports that this occurs in patients, as well.

In one embodiment, an exemplary protocol is as follows. Infrared light in the wavelength range of 200-2000 nm of a power range of 00.01-50.00 watts is applied to the skin over the area or structure to be treated. The infrared light emitter device is set to protocols specific to the condition and to the patient. Variations in the use of continuous or pulsed light, type and rate of pulsing, wavelengths, duration, and power density are included in this methodology. Variations in the light emitter device would include stationary, hand-held mobile, hand-held stationary, computer-controlled mobile and computer-controlled stationary configurations, depending on the embodiment and the particular patient needs. The patient is positioned to be comfortable and so that the area to be treated is fully accessible. The patient and the operator wear protective safety gear such as eyewear. If the area to be treated is the brain, then the hair on the overlying scalp must be cut to less than ½ inch or shaved. The operator applies the infrared light applicator directly to or very close to the skin of the patient. A continuous motion must be maintained to minimize heating and/or patient discomfort. A sweeping or scanning action also facilitates covering large areas to be treated. Dosing is dependent on area to be treated, wattage, pulsing, duration, and distance from the skin. Infrared application is continued for the duration of treatment appropriate to the area/structure to be treated. Temperature is monitored by laser thermometer or other light/heat meter monitor device. Duration of treatment varies depending on area to be treated, patient parameters, and therapeutic response. For most conditions, multiple treatments are required. These treatments are conducted at intervals not less than every 48 hours. Protocols for TBI, IPD, ADSD, PTSD, DA, MS, SCI, PNL, RDL, STR, MTD and other diseases, conditions, and dysfunction are distinct and disease-specific. Conditions involving different areas of the body have distinct methodologies. Coincidentally, sequentially, or in temporal proximity, the patient receives administration(s) of ketamine. In one embodiment, this could be intravenous infusions over a prolonged interval of 20-90 minutes. The patient is appropriately prepared and an intravenous line is placed. One embodiment would include monitoring of ECG, blood pressure and pulse oximetry is maintained for patient safety. In certain embodiments, ketamine is infused at a dose of 0.2-5.0 mg/kg, depending upon the embodiment. In other embodiments, ketamine is administered orally, intranasally, or intra-muscularly at intervals ranging from hours to days, depending on the embodiment. Ketamine has been shown to upregulate BDNF by a number of molecular pathways.

While particular embodiments have been described and disclosed in the present application, it is clear that any number of permutations, modifications, or embodiments may be made without departing from the spirit and the scope of this disclosure.

Particular terminology used when describing certain features or aspects of the embodiments should not be taken to imply that the terminology is being redefined herein to be restricted to any specific characteristics, features, or aspects with which that terminology is associated. In general, the terms used in the following claims should not be construed to be limited to the specific embodiments disclosed in the specification, unless the above Detailed Description section explicitly defines such terms. Accordingly, the actual scope of the claims encompasses not only the disclosed embodiments, but also all equivalent ways of practicing or implementing the claimed subject matter.

The above detailed description of the embodiments is not intended to be exhaustive or to limit the disclosure to the precise embodiment or form disclosed herein or to the particular fields of usage mentioned above. While specific embodiments and examples are described above for illustrative purposes, various equivalent modifications are possible within the scope of the disclosure, as those skilled in the relevant art will recognize. Also, the teachings of the embodiments provided herein can be applied to other systems, not necessarily the system described above. The elements and acts of the various embodiments described above can be combined to provide further embodiments.

Any patents, applications and other references that may be listed in accompanying or subsequent filing papers, as well as those listed above, are incorporated herein by reference in their entirety. Aspects of embodiments can be modified, if necessary, to employ the systems, functions, and concepts of the various references to provide yet further embodiments.

In light of the above "Detailed Description," the inventors may make changes to the disclosure. While the detailed description outlines possible embodiments and discloses the best mode contemplated, no matter how detailed the above appears in text, embodiments may be practiced in a myriad of ways. Thus, implementation details may vary considerably while still being encompassed by the spirit of the embodiments as disclosed by the inventors. As discussed herein, specific terminology used when describing certain features or aspects should not be taken to imply that the terminology is being redefined herein to be restricted to any specific characteristics, features, or aspects of the embodiments with which that terminology is associated.

While certain aspects are presented below in certain claim forms, the inventors contemplate the various aspects in any number of claim forms. Accordingly, the inventors reserve the right to add additional claims after filing the application to pursue such additional claim forms for other aspects.

The above specification, examples and data provide a description of the structure and use of exemplary implementations of the described systems, articles of manufacture and methods. It is important to note that many implementations can be made without departing from the spirit and scope of the disclosure.

The invention claimed is:

1. A method of treating certain neurological disorders arising from neurotrophin deficiency and/or mitochondrial dysfunction comprising the steps of:
   locating a brain lesion to be treated;
   administering a dose of ketamine to a patient in an amount of 0.01-10 mg/kg of patient body weight; and
   applying light having a wavelength between 600 and 1,200 nm and a power of 10.1-30 W to the scalp of the patient toward the brain lesion.

2. The method of claim 1 wherein the dose of ketamine is 5 mg per kg of the patient's body weight or less.

3. The method of claim 2 wherein the dose of ketamine is 1 mg per kg of the patient's body weight or less.

4. The method of claim 3 wherein the dose of ketamine is 0.5 mg per kg of the patient's body weight or less.

5. The method of claim 1 wherein the infrared light applied to the scalp of the patient has a total fluence greater than 10 J/cm$^2$.

6. The method of claim 1 wherein the infrared light applied to the scalp of the patient has a total fluence between 55 and 81 J/cm$^2$.

7. The method of claim 1 further comprising the steps of:
   obtaining at least one medical image of the patient's brain;
   analyzing the image to identify the lesion;
   targeting the application of infrared light to the lesion.

8. The method of claim 7 wherein the infrared light has a total fluence of 0.64-1.95 J/cm² at the lesion so targeted.

9. The method of claim 1 wherein the infrared light is coherent.

10. The method of claim 1 wherein the infrared light has a wavelength between 800 and 1000 nm.

11. The method of claim 10 wherein the light has a wavelength of 810 nanometers.

12. The method of claim 10 wherein the light has a wavelength of 980 nanometers.

13. The method of claim 10 wherein the light consists of two wavelengths: 810 and 980 nanometers.

14. The method of claim 1 where in the light is pulsed.

15. The method of claim 14 wherein the light is pulsed at greater than 1 Hz.

16. The method of claim 15 wherein the light is pulsed at greater than 10 Hz.

17. The method of claim 16 wherein the light is pulsed at greater than 100 Hz.

18. The method of claim 1 wherein a duty cycle of the pulses is at least 10%.

19. The method of claim 1 wherein a duty cycle of the pulses is 50%.

20. The method of claim 1, further comprising the step of administering a dietary supplement.

21. The method of claim 20, wherein the dietary supplement is selected from a group consisting of:
   a. acetyl-L-carnitine;
   b. Omega-3 fatty acids;
   c. cerebrolysin;
   d. low dose lithium;
   e. natural anthocyanins;
   f. *Gingko biloba;*
   g. vinpocetine; and
   h. huperzine.

22. The method of claim 20, wherein the dietary supplement comprises natural anthocyanins.

23. The method of claim 1, further comprising the step of instructing the patient on physical exercises to be performed.

24. The method of claim 23, wherein the exercises to be performed are designed to improve balance and coordination.

25. The method of claim 24 wherein the exercises to be performed comprise two or more Parkinson Exercises and Rehabilitation Klass ("PERKS") exercises.

26. The method of claim 25, wherein the exercises to be performed comprise the entirety of the PERKS program.

27. The method of claim 1, wherein the neurological disorder is Traumatic Brain Injury, mild-to-moderate stroke, Idiopathic Parkinson's Disease, Alzheimer's Disease, Senility, Dementia, Neurodegeneration, Multiple Sclerosis, depression, pain, or anxiety of the patient.

* * * * *